US012370189B2

(12) United States Patent
Cavatur et al.

(10) Patent No.: US 12,370,189 B2
(45) Date of Patent: *Jul. 29, 2025

(54) PHARMACEUTICAL FORMULATION

(71) Applicant: RB HEALTH (US) LLC, Parsippany, NJ (US)

(72) Inventors: Raghu Cavatur, Parsippany, NJ (US); Kevin Chen, Parsippany, NJ (US); Matthew James Kaser, Parsippany, NJ (US); Hongchun Qiu, Basking Ridge, NJ (US)

(73) Assignee: RB HEALTH (US) LLC, Parsippany, NJ (US)

( * ) Notice: Subject to any disclaimer, the term of this patent is extended or adjusted under 35 U.S.C. 154(b) by 390 days.

This patent is subject to a terminal disclaimer.

(21) Appl. No.: 17/486,225

(22) Filed: Sep. 27, 2021

(65) Prior Publication Data

US 2022/0079937 A1 Mar. 17, 2022

Related U.S. Application Data

(63) Continuation of application No. 15/520,752, filed as application No. PCT/GB2015/053151 on Oct. 21, 2015, now abandoned.

(60) Provisional application No. 62/066,532, filed on Oct. 21, 2014.

(30) Foreign Application Priority Data

Apr. 21, 2015 (GB) ...................... 1506755

(51) Int. Cl.
| | | |
|---|---|---|
| *A61K 31/485* | (2006.01) | |
| *A61K 9/20* | (2006.01) | |
| *A61K 9/24* | (2006.01) | |
| *A61K 31/09* | (2006.01) | |
| *A61K 31/137* | (2006.01) | |
| *A61K 31/192* | (2006.01) | |
| *A61K 45/06* | (2006.01) | |
| *A61K 47/02* | (2006.01) | |
| *A61K 47/12* | (2006.01) | |
| *A61K 47/20* | (2006.01) | |
| *A61K 47/26* | (2006.01) | |
| *A61K 47/32* | (2006.01) | |
| *A61K 47/36* | (2006.01) | |
| *A61K 47/38* | (2006.01) | |

(52) U.S. Cl.
CPC .......... *A61K 31/485* (2013.01); *A61K 9/2054* (2013.01); *A61K 9/209* (2013.01); *A61K 31/09* (2013.01); *A61K 31/137* (2013.01); *A61K 31/192* (2013.01); *A61K 45/06* (2013.01); *A61K 47/02* (2013.01); *A61K 47/12* (2013.01); *A61K 47/20* (2013.01); *A61K 47/26* (2013.01); *A61K 47/32* (2013.01); *A61K 47/36* (2013.01); *A61K 47/38* (2013.01)

(58) Field of Classification Search
CPC .. A61K 31/137; A61K 31/192; A61K 31/485; A61K 2300/00; A61K 47/12; A61K 47/20; A61K 47/38
See application file for complete search history.

(56) References Cited

U.S. PATENT DOCUMENTS

| | | | |
|---|---|---|---|
| 2,738,303 | A | 3/1956 | Blythe |
| 2,951,792 | A | 9/1960 | Swintosky |
| 3,065,143 | A | 11/1962 | Christenson et al. |
| 3,362,880 | A | 1/1968 | Sampson |
| 3,362,881 | A | 1/1968 | Klaus et al. |
| 3,458,622 | A | 7/1969 | Hill |
| 3,555,151 | A | 1/1971 | Kaplan et al. |
| 3,558,768 | A | 1/1971 | Klippel |
| 3,634,584 | A | 1/1972 | Poole |
| 3,870,790 | A | 3/1975 | Lowey et al. |
| 3,981,984 | A | 9/1976 | Signorino |
| 4,122,157 | A | 10/1978 | Huber |
| 4,140,755 | A | 2/1979 | Sheth et al. |
| 4,167,558 | A | 9/1979 | Sheth et al. |
| 4,226,849 | A | 10/1980 | Schor |
| 4,248,857 | A | 2/1981 | DeNeale et al. |
| 4,248,858 | A | 2/1981 | Guley et al. |
| 4,259,314 | A | 3/1981 | Lowey |
| 4,308,251 | A | 12/1981 | Dunn et al. |
| 4,309,404 | A | 1/1982 | DeNeale et al. |
| 4,309,405 | A | 1/1982 | Guley |
| 4,357,469 | A | 11/1982 | Schor |
| 4,369,172 | A | 1/1983 | Schor et al. |

(Continued)

FOREIGN PATENT DOCUMENTS

| | | |
|---|---|---|
| CN | 201257161 Y | 6/2009 |
| CN | 202211874 U | 5/2012 |

(Continued)

OTHER PUBLICATIONS

*Adams Respiratory Therapeutics, Inc., et al.* v. *Perrigo Company, et al.*, Defendants' Reply Memorandum In Support of Their Motion for Summary Judgment of Non-Infringement (W.D. Mich. Dec. 28, 2009).

*Adams Respiratory Therapeutics, Inc., et al.* v. *Perrigo Company, et al.*, Opinion [regarding Plaintiffs' motion for reconsideration and Defendants' motion for summary judgment] (W.D. Mich. Feb. 11, 2010).

*Adams Respiratory Therapeutics, Inc., et al.* v. *Perrigo Company, et al.*, Order Reconsidering and Vacating In Part Opinion and Order Regarding Claim Construction (W.D. Mich. Mar. 3, 2010).

(Continued)

*Primary Examiner* — Dominic Lazaro
(74) *Attorney, Agent, or Firm* — VENABLE LLP

(57) ABSTRACT

The present invention is directed to a pharmaceutical composition comprising a pharmaceutically effective amount of guaifenesin, naproxen and at least one further active which is selected to be an antitussive, a decongestant or an antihistamine.

8 Claims, No Drawings

(56) References Cited

U.S. PATENT DOCUMENTS

| | | |
|---|---|---|
| 4,389,393 A | 6/1983 | Schor et al. |
| 4,424,235 A | 1/1984 | Sheth et al. |
| 4,540,566 A | 9/1985 | Davis et al. |
| 4,543,370 A | 9/1985 | Porter et al. |
| 4,552,899 A | 11/1985 | Sunshine et al. |
| 4,619,934 A | 10/1986 | Sunshine et al. |
| 4,680,323 A | 7/1987 | Lowey |
| 4,695,464 A | 9/1987 | Alderman |
| 4,699,779 A | 10/1987 | Palinczar |
| 4,704,285 A | 11/1987 | Alderman |
| 4,738,966 A | 4/1988 | Sunshine et al. |
| 4,749,697 A | 6/1988 | Sunshine et al. |
| 4,749,711 A | 6/1988 | Sunshine et al. |
| 4,749,720 A | 6/1988 | Sunshine et al. |
| 4,749,721 A | 6/1988 | Sunshine et al. |
| 4,749,722 A | 6/1988 | Sunshine et al. |
| 4,749,723 A | 6/1988 | Sunshine et al. |
| 4,756,911 A | 7/1988 | Drost |
| 4,795,643 A | 1/1989 | Seth |
| 4,798,725 A | 1/1989 | Patel |
| 4,814,179 A | 3/1989 | Bolton et al. |
| 4,826,688 A | 5/1989 | Panoz |
| 4,834,965 A | 5/1989 | Martani et al. |
| 4,834,984 A | 5/1989 | Goldie et al. |
| 4,839,354 A | 6/1989 | Sunshine et al. |
| 4,851,392 A | 7/1989 | Shaw et al. |
| 4,871,548 A | 10/1989 | Edgren et al. |
| 4,900,557 A | 2/1990 | Dell et al. |
| 4,920,149 A | 4/1990 | Sunshine et al. |
| 4,968,508 A | 11/1990 | Oren et al. |
| 4,971,805 A | 11/1990 | Kitanishi et al. |
| 4,980,170 A | 12/1990 | Schneider et al. |
| 4,983,398 A | 1/1991 | Gaylord et al. |
| 4,990,341 A | 2/1991 | Goldie et al. |
| 4,994,276 A | 2/1991 | Baichwal et al. |
| 5,004,613 A | 4/1991 | Radebaugh et al. |
| 5,032,406 A | 7/1991 | Dansereau |
| 5,047,248 A | 9/1991 | Calanchi et al. |
| 5,085,865 A | 2/1992 | Nayak |
| 5,098,715 A | 3/1992 | McCabe et al. |
| 5,133,974 A | 7/1992 | Paradissis |
| 5,164,398 A | 11/1992 | Sims et al. |
| 5,186,943 A | 2/1993 | Okada et al. |
| 5,186,963 A | 2/1993 | Howman |
| 5,200,193 A | 4/1993 | Radebaugh et al. |
| 5,260,073 A | 11/1993 | Phipps |
| 5,286,493 A | 2/1994 | Oshlack et al. |
| 5,292,534 A | 3/1994 | Valentine et al. |
| 5,326,571 A | 7/1994 | Wright et al. |
| 5,358,717 A | 10/1994 | Kuramoto et al. |
| 5,368,861 A | 11/1994 | Ushimaru et al. |
| 5,376,384 A | 12/1994 | Eichel et al. |
| 5,395,626 A | 3/1995 | Kotwal et al. |
| 5,403,593 A | 4/1995 | Royce |
| 5,427,799 A | 6/1995 | Valentine et al. |
| 5,445,829 A | 8/1995 | Paradissis et al. |
| 5,451,409 A | 9/1995 | Rencher et al. |
| 5,470,580 A | 11/1995 | Kuramoto et al. |
| 5,472,704 A | 12/1995 | Santus et al. |
| 5,486,364 A | 1/1996 | King et al. |
| 5,494,681 A | 2/1996 | Cuca et al. |
| 5,529,791 A | 6/1996 | Deboeck et al. |
| 5,576,022 A | 11/1996 | Yang et al. |
| 5,593,694 A | 1/1997 | Hayashida |
| 5,650,169 A | 7/1997 | Conte et al. |
| 5,656,296 A | 8/1997 | Khan |
| 5,662,933 A | 9/1997 | Baichwal et al. |
| 5,738,874 A | 4/1998 | Conte et al. |
| 5,773,031 A | 6/1998 | Shah et al. |
| 5,773,032 A | 6/1998 | Engel |
| 5,780,057 A | 7/1998 | Conte et al. |
| 5,807,580 A | 9/1998 | Luber |
| 5,840,329 A | 11/1998 | Bai |
| 5,859,060 A | 1/1999 | Platt |
| 5,945,123 A | 8/1999 | Hermelin |
| 5,968,554 A | 10/1999 | Beiman et al. |
| 5,993,858 A | 11/1999 | Crison et al. |
| 6,120,802 A | 9/2000 | Breitenbach et al. |
| 6,165,506 A | 12/2000 | Jain et al. |
| 6,210,710 B1 | 4/2001 | Skinner |
| 6,217,903 B1 | 4/2001 | Skinner |
| 6,217,904 B1 | 4/2001 | Midha et al. |
| 6,294,199 B1 | 9/2001 | Conley |
| 6,312,724 B1 | 11/2001 | Odidi et al. |
| 6,340,476 B1 | 1/2002 | Midha et al. |
| 6,372,252 B1 | 4/2002 | Blume |
| 6,372,254 B1 | 4/2002 | Ting et al. |
| 6,475,521 B1 | 11/2002 | Timmins et al. |
| 6,555,136 B2 | 4/2003 | Midha |
| 6,623,756 B1 | 9/2003 | Wilber et al. |
| 6,730,321 B2 | 5/2004 | Ting et al. |
| 6,838,094 B2 | 1/2005 | Grimmett et al. |
| 6,955,821 B2 | 10/2005 | Davis |
| 7,838,032 B2 | 11/2010 | Davis |
| 8,999,388 B2 | 4/2015 | Lim et al. |
| 9,023,390 B2 | 5/2015 | Wertz et al. |
| 9,066,942 B2 | 6/2015 | Giliyar et al. |
| 9,149,533 B2 | 10/2015 | Guido et al. |
| 9,220,704 B2 | 12/2015 | Kim et al. |
| 9,456,985 B2 | 10/2016 | Wertz et al. |
| 9,545,448 B2 | 1/2017 | Guido et al. |
| 9,572,780 B2 | 2/2017 | Lim et al. |
| 9,579,389 B2 | 2/2017 | Guido et al. |
| 9,655,971 B2 | 5/2017 | Guido et al. |
| 9,662,399 B2 | 5/2017 | Guido et al. |
| 10,478,504 B2 | 11/2019 | Guido et al. |
| 10,576,041 B2 | 3/2020 | Stella et al. |
| 10,792,364 B2 | 10/2020 | Guido et al. |
| 11,278,506 B2 * | 3/2022 | Cavatur ............ A61K 31/192 |
| 11,433,030 B2 | 9/2022 | Stella et al. |
| 11,576,974 B2 | 2/2023 | Guido et al. |
| 11,813,361 B2 | 11/2023 | Mohammad |
| 2002/0022058 A1 | 2/2002 | Lovercheck |
| 2002/0058061 A1 | 5/2002 | Midha et al. |
| 2002/0142044 A1 | 10/2002 | Vendola |
| 2002/0164371 A1 | 11/2002 | Ting et al. |
| 2003/0012820 A1 | 1/2003 | Upadhyay |
| 2003/0039691 A1 | 2/2003 | Waterman |
| 2003/0049318 A1 * | 3/2003 | Davis ................ A61K 31/485 |
| | | 424/468 |
| 2003/0091624 A1 | 5/2003 | Szymczak et al. |
| 2003/0147952 A1 | 8/2003 | Lim et al. |
| 2003/0180352 A1 | 9/2003 | Patel |
| 2003/0194439 A1 | 10/2003 | Midha et al. |
| 2003/0215508 A1 | 11/2003 | Davis et al. |
| 2004/0022851 A1 | 2/2004 | Davis et al. |
| 2004/0033258 A1 | 2/2004 | Koike |
| 2004/0156902 A1 | 8/2004 | Lee et al. |
| 2004/0180085 A1 | 9/2004 | Ohkouchi et al. |
| 2005/0013863 A1 | 1/2005 | Lim et al. |
| 2005/0095288 A1 | 5/2005 | Honea |
| 2005/0152967 A1 | 7/2005 | Tengler et al. |
| 2005/0276852 A1 | 12/2005 | Davis et al. |
| 2006/0127473 A1 | 6/2006 | Nichols |
| 2007/0134317 A1 | 6/2007 | Gruber |
| 2008/0014274 A1 | 1/2008 | Bubnis et al. |
| 2009/0202633 A1 | 8/2009 | Velaga et al. |
| 2012/0201887 A1 | 8/2012 | Ahlgren et al. |
| 2012/0252833 A1 | 10/2012 | Wertz et al. |
| 2012/0263792 A1 | 10/2012 | Lim et al. |
| 2013/0172381 A1 | 7/2013 | Giliyar et al. |
| 2014/0179728 A1 | 6/2014 | Giliyar et al. |
| 2014/0179729 A1 | 6/2014 | Giliyar et al. |
| 2014/0186515 A1 | 7/2014 | Lim et al. |
| 2014/0221416 A1 | 8/2014 | Guido et al. |
| 2014/0227356 A1 | 8/2014 | Kim et al. |
| 2015/0098992 A1 | 4/2015 | Kim et al. |
| 2015/0196555 A1 | 7/2015 | Guido et al. |
| 2015/0196556 A1 | 7/2015 | Guido et al. |
| 2015/0196557 A1 | 7/2015 | Guido et al. |
| 2015/0202300 A1 | 7/2015 | Guido et al. |
| 2015/0238423 A1 | 8/2015 | Wertz et al. |
| 2015/0283084 A1 | 10/2015 | Mohammad |
| 2015/0320686 A1 | 11/2015 | Giliyar et al. |

(56) References Cited

U.S. PATENT DOCUMENTS

| | | |
|---|---|---|
| 2016/0030352 A1 | 2/2016 | Lim et al. |
| 2016/0256454 A1 | 9/2016 | Giliyar et al. |
| 2017/0100355 A1 | 4/2017 | Cavatur et al. |
| 2017/0202817 A1 | 7/2017 | Lim et al. |
| 2017/0296671 A1 | 10/2017 | Guido et al. |
| 2017/0304210 A1 | 10/2017 | Ahlgren et al. |
| 2017/0304296 A1 | 10/2017 | Cavatur et al. |
| 2018/0071277 A1 | 3/2018 | Giliyar et al. |
| 2018/0085317 A1 | 3/2018 | Stella et al. |
| 2019/0209551 A1 | 7/2019 | Giliyar et al. |
| 2019/0240333 A1 | 8/2019 | Guido et al. |
| 2020/0113841 A1 | 4/2020 | Stella et al. |
| 2020/0261373 A1 | 8/2020 | Ahlgren et al. |
| 2020/0390892 A1 | 12/2020 | Guido et al. |
| 2023/0293695 A1 | 9/2023 | Guido et al. |
| 2024/0180839 A1 | 6/2024 | Mohammad |

FOREIGN PATENT DOCUMENTS

| | | |
|---|---|---|
| EP | 0409781 B1 | 6/1994 |
| EP | 0 875 245 A2 | 9/1999 |
| GB | 2255344 A | 11/1992 |
| JP | 7277962 | 10/1995 |
| JP | 2001-187737 A | 7/2001 |
| WO | 85/04589 A1 | 10/1985 |
| WO | 87/00044 | 1/1987 |
| WO | 91/17746 A1 | 11/1991 |
| WO | 92/04022 A1 | 3/1992 |
| WO | 94/06416 A1 | 3/1994 |
| WO | 94/27557 A2 | 12/1994 |
| WO | 95/19759 A1 | 7/1995 |
| WO | 95/20946 A1 | 8/1995 |
| WO | 95/28148 A1 | 10/1995 |
| WO | 96/04908 A1 | 2/1996 |
| WO | 97/09042 A1 | 3/1997 |
| WO | 98/05305 A1 | 2/1998 |
| WO | 98/22091 A1 | 5/1998 |
| WO | 98/22097 | 5/1998 |
| WO | 99/17745 A1 | 4/1999 |
| WO | 00/10537 A1 | 3/2000 |
| WO | 00/33818 A1 | 6/2000 |
| WO | 00/59479 A1 | 10/2000 |
| WO | 01/19901 A2 | 3/2001 |
| WO | 2003/088952 A1 | 10/2003 |
| WO | 2010/121326 A1 | 10/2010 |
| WO | 2013/055177 A1 | 4/2013 |
| WO | 2013/154390 A1 | 10/2013 |
| WO | 2016/063055 A1 | 4/2016 |

OTHER PUBLICATIONS

*Adams Respiratory Therapeutics, Inc., et al. v. Perrigo Company, et al.*, Non-Confidential Brief of Plaintiffs—Appellants Adams Respiratory Therapeutics, Inc., Adams Respiratory Operations, Inc., and Adams Respiratory Products, Inc. (Fed. Cir. Mar. 24, 2010).
*Adams Respiratory Therapeutics, Inc., et al. v. Perrigo Company, et al.*, NonConfidential Brief For Defendants—Appellees (Fed. Cir. Apr. 23, 2010).
*Adams Respiratory Therapeutics, Inc., et al. v. Perrigo Company, et al.*, Non-Confidential Reply Brief of Plaintiffs—Appellants (Fed. Cir. May 3, 2010).
*Adams Respiratory Therapeutics, Inc., et al. v. Perrigo Company, et al.*, Opinion (Fed. Cir. Aug. 5, 2010).
Drituss G and Q-Bid LA, Qualitest 011, produced by Perrigo Company et al. in the *Adams Respiratory Therapeutics, Inc. et al. v. Perrigo Company et al.* (W.D. Mich.) litigation in Aug. 2008.
Drituss G and Q-Bid LA, Vintage 011, produced by Perrigo Company et al. in the *Adams Respiratory Therapeutics, Inc. et al. v. Perrigo Company et al.* (W.D. Mich.) litigation in Aug. 2008.
Drituss G label, Vintage 012, Dec. 2001.
Drituss G label, Vintage 013, Dec. 2001.
Guaifenesin Long-Acting Tablets, Vintage 014, Dec. 2001.
Guaifenesin Sustained-Release Tablets and Guaifenesin/Dextromethorphan Hydrobromide Sustained-Release Tablets, Vintage 018, Mar. 2001.
Q-Bid LA label, Qualitest 015, Apr. 1994.
Q-Bid LA label, Qualitest 017, May 1999.
Q-Bid LA label, Vintage 015, Apr. 1994.
Q-Bid LA label, Vintage 016, Feb. 1999.
Q-Bid LA label, Vintage 017, May 1999.
*Reckitt Benckiser Inc. v. Watson Laboratories, Inc.—Florida & Watson Pharmaceuticals, Inc.*, Amended Complaint For Patent Infringement (S.D. Fla. Oct. 23, 2009).
*Reckitt Benckiser Inc. v. Watson Laboratories, Inc.—Florida & Watson Pharmaceuticals, Inc.*, Defendants Watson Laboratories, Inc.—Florida and Watson Pharmaceuticals, Inc.'s Answer and Counterclaims to Plaintiff's Amended Complaint (S.D. Fla. Oct. 29, 2009).
*Reckitt Benckiser Inc. v. Watson Laboratories, Inc.—Florida & Watson Pharmaceuticals, Inc.*, Reckitt Benckiser's Answer to Watson Laboratories, Inc.—Florida and Watson Pharmaceuticals, Inc.'s Oct. 29, 2009 Counterclaims (S.D. Fla. Nov. 23, 2009).
Physicians' Desk Reference: For Nonprescription Drugs and Dietary Supplements 807 (Medical Economics Company, Inc., 20th ed. 1999).
Bauer et al., "Coated Pharmaceutical Dosage Forms," p. 83 (MedPharm Scientific Publishers 1998).
Request for Reexamination, filed Apr. 20, 2005, U.S. Pat. No. 6,372,252, Issued Apr. 16, 2002.
Welling, P.G., "Oral Controlled Drug Administration: Pharmacokinetic Considerations," Drug Dev. Ind. Pharm., 9, 1185-1225 (1983).
International Search Report dated Aug. 19, 2003 for International Application No. PCT/US03/11500, filed Apr. 15, 2003.
Bodmeier, R. et al., "Prolonged Release Multiple-Unit Dosage Forms Based on Water-Soluble Cellulosic Polymers or Aqueous Latexes," Proceed. Intern. Sump. Control. Rel. Bioact. Mater., 18 (1991), Controlled Release Society, Inc.
Lacy et al. Drug Information Handbook p. 481 (1999).
Ansel HC and Popovich NG, Pharmaceutical Dosage Forms and Drug Delivery Systems, Lea & Febiger, p. 64 (5th ed. 1990).
Bankser GS and Rhodes CT, Modern Pharmaceutics, Marcel Dekker, Inc., p. 83 (4th ed. 2002).
United Research Laboratories and Mutual Pharmaceutical Company, Press Release: United Research Laboratories/Mutual Pharmaceutical Company Announce ANDA Filing For Guaifenesin Extended-Release Tablets, 600 mg and 1200 mg (Aug. 18, 2006).
Correspondence from E. Brendan Magrab, Esq., Vice President, Intellectual Property, United Research Laboratories, Inc. and Mutual Pharmaceutical Company, Inc. to Michael J. Valentino, President & Chief Executive Officer, Adams Respiratory Therapeutics, Inc., including Exhibits A and B and additional attachments (Aug. 22, 2006).
United Research Laboratories and Mutual Pharmaceutical Company, Press Release: United Research Laboratories/Mutual Pharmaceutical Company Formally Notifies Adams Respiratory Therapeutics of Its ANDA Filing For Guaifenesin Extended-Release Tablets, 600 mg and 1200 mg (Aug. 23, 2006).
Correspondence from Joseph M. O'Malley, Jr., Esq., Attorney, Fitzpatrick, Cella, Harper & Scinto to E. Brendan Magrab, Esq., Vice President, Intellectual Property, United Research Laboratories, Inc. and Mutual Pharmaceutical Company, Inc., including attachment (Aug. 31, 2006).
Correspondence from James D. Veltrop, Attorney, Axinn, Veltrop & Harkrider LLP to Joseph M. O'Malley, Jr., Esq., Attorney, Fitzpatrick, Cella, Harper & Scinto, including attachment (Sep. 6, 2006).
United Research Laboratories and Mutual Pharmaceutical Company, Press Release: United Research Laboratories/Mutual Pharmaceutical Company Views Legal Response From Adams as Excessive and Disengenuous [sic] Attempt to Delay Competition (Sep. 7, 2006).
Correspondence from James D. Veltrop, Attorney, Axinn, Veltrop & Harkrider LLP to Dominick A. Conde, Attorney, Fitzpatrick, Cella, Harper & Scinto (Sep. 28, 2006).
Declaration of Harry G. Brittain, Ph.D. (Sep. 28, 2006), available at http://www.urlmutual.com/guaifenesin7.pdf.

(56) References Cited

OTHER PUBLICATIONS

United Research Laboratories and Mutual Pharmaceutical Company, Press Release: Independent Expert Confirms View That Adams Has No Legal Basis for Pursuing Legal Action Against Mutual Pharmaceutical Company for Its Guaifenesin Extended Release Tablets, 600 mg and 1200 mg (Sep. 28, 2006).
*Adams Respiratory Therapeutics, Inc.* v. *Pharmaceutical Holdings Corp.*, Complaint for Patent Infringement and Certification Pursuant to Local Rule 11.2, including Exhibit A (D.N.J. Oct. 2, 2006).
*Adams Respiratory Therapeutics, Inc.* v. *Pharmaceutical Holdings Corp.*, Complaint for Patent Infringement, including Exhibit A (E.D. Pa. Oct. 4, 2006).
*Adams Respiratory Therapeutics, Inc.* v. *Pharmaceutical Holdings Corp.*, Answer and Counterclaims (E.D. Pa. Oct. 10, 2006).
*Adams Respiratory Therapeutics, Inc.* v. *Pharmaceutical Holdings Corp.*, Defendants' Motion for Summary Judgment (E.D. Pa. Oct. 17, 2006).
*Adams Respiratory Therapeutics, Inc.* v. *Pharmaceutical Holdings Corp.*, Defendants' Memorandum of Law in Support of a Motion for Summary Judgment (E.D. Pa. Oct. 17, 2006).
United Research Laboratories and Mutual Pharmaceutical Company, Press Release: Mutual Pharmaceutical Company Files Counter Suit Against Adams Respiratory Therapeutics (Oct. 17, 2006).
U.S. Department of Health and Human Services, Approved Drug Products with Therapeutic Equivalence Evaluations, pp. ix-x (19th ed. 1999).
*Adams Respiratory Therapeutics, Inc., et al.* v. *Perrigo Company, et al.*, Docket Entries (W.D. Mich.), 2020.
*Adams Respiratory Therapeutics, Inc., et al.* v. *Perrigo Company, et al.*, Opinion (W.D. Mich. Jan. 11, 2012).
*Reckitt Benckiser Inc.* v. *Watson Laboratories, Inc.—Florida & Watson Pharmaceuticals, Inc.*, Docket Entries (S.D. Fla.), 2020.
*Reckitt Benckiser Inc.* v. *Watson Laboratories, Inc.—Florida & Watson Pharmaceuticals, Inc.*, Plaintiff Reckitt's Responses to Defendant Watson Laboratories, Inc.—Florida's First Set of Interrogatories (Nos. 1-4) (S.D. Fla. Oct. 19, 2009).
*Reckitt Benckiser Inc.* v. *Watson Laboratories, Inc.—Florida & Watson Pharmaceuticals, Inc.*, Plaintiff Reckitt's Supplemental Responses to Defendant Watson Laboratories, Inc.—Florida's First Set of Interrogatories (Nos. 1-4) (S.D. Fla. May 19, 2010).
*Reckitt Benckiser Inc.* v. *Watson Laboratories, Inc.—Florida & Watson Pharmaceuticals, Inc.*, Defendant Watson Laboratories, Inc.—Florida's Declaration of Gilbert S. Banker in Support of Watson Florida's Claim Construction Brief (S.D. Fla. Sep. 10, 2010).
*Reckitt Benckiser Inc.* v. *Watson Laboratories, Inc.—Florida & Watson Pharmaceuticals, Inc.*, Defendant Watson Laboratories, Inc.—Florida's Claim Construction Brief (S.D. Fla. Sep. 10, 2010).
*Reckitt Benckiser Inc.* v. *Watson Laboratories, Inc.—Florida & Watson Pharmaceuticals, Inc.*, Defendant Watson Laboratories, Inc.—Florida's Declaration of Thomas Dowling in Support of Defendant Watson Florida's Claim Construction Brief (S.D. Fla. Sep. 10, 2010).
*Reckitt Benckiser Inc.* v. *Watson Laboratories, Inc.—Florida & Watson Pharmaceuticals, Inc.*, Supplemental Declaration of Dr. Thomas Foster (S.D. Fla. Sep. 24, 2010).
*Reckitt Benckiser Inc.* v. *Watson Laboratories, Inc.—Florida & Watson Pharmaceuticals, Inc.*, Declaration of Dr. Gordon Amidon (S.D. Fla. Sep. 24, 2010).
*Reckitt Benckiser Inc.* v. *Watson Laboratories, Inc.—Florida & Watson Pharmaceuticals, Inc.*, Defendant Watson Laboratories, Inc.—Florida's Supplemental Declaration of Thomas Dowling in Support of Defendant Watson Florida's Reply in Support of Claim Construction Brief (S.D. Fla. Oct. 1, 2010).
*Reckitt Benckiser Inc.* v. *Watson Laboratories, Inc.—Florida & Watson Pharmaceuticals, Inc.*, Defendant Watson Laboratories, Inc.—Florida's Reply in Support of Claim Construction Brief (S.D. Fla. Oct. 1, 2010).
*Reckitt Benckiser Inc.* v. *Watson Laboratories, Inc.—Florida & Watson Pharmaceuticals, Inc.*, Reckitt's Memorandum In Support of Its Motion for Summary Judgment of No Inequitable Conduct—Redacted (S.D. Fla. Nov. 12, 2010).
*Reckitt Benckiser Inc.* v. *Watson Laboratories, Inc.—Florida & Watson Pharmaceuticals, Inc.*, Watson Laboratories, Inc.—Florida's Motion for Summary Judgment of Non-Infringement and Supporting Memorandum of Law (S.D. Fla. Nov. 12, 2010).
*Reckitt Benckiser Inc.* v. *Watson Laboratories, Inc.—Florida & Watson Pharmaceuticals, Inc.*, Order Approving Notices of Withdrawal; Withdrawing Motions (S.D. Fla. Dec. 6, 2010).
*Reckitt Benckiser Inc.* v. *Watson Laboratories, Inc.—Florida & Watson Pharmaceuticals, Inc.*, Claim Construction Order (S.D. Fla. Jan. 12, 2011).
*Reckitt Benckiser Inc.* v. *Watson Laboratories, Inc.—Florida & Watson Pharmaceuticals, Inc.*, Final Judgment for Defendant (S.D. Fla. Feb. 9, 2011).
*Reckitt Benckiser Inc.* v. *Watson Laboratories, Inc.—Florida & Watson Pharmaceuticals, Inc.*, Watson Laboratories, Inc.—Florida of Proposed Redacted Findings of Fact and Conclusions of Law (S.D. Fla. Feb. 16, 2011).
*Reckitt Benckiser Inc.* v. *Watson Laboratories, Inc.*, Opinion (Fed. Cir. Jul. 7, 2011).
*Reckitt Benckiser LLC* v. *Perrigo Company and Perrigo Research and Development Company*, Complaint for Patent Infringement (D.N.J. Mar. 26, 2015).
*Reckitt Benckiser LLC* v. *Perrigo Company and Perrigo Research and Development Company*, Consent Judgment and Stipulation of Dismissal (D.N.J. Aug. 6, 2015).
*Reckitt Benckiser LLC* v. *Dr. Reddy's Laboratories, Inc.*, Docket Entries (D.N.J.), 2020.
*Reckitt Benckiser LLC* v. *Dr. Reddy's Laboratories, Inc. and Dr. Reddy's Laboratories, Ltd.*, Complaint for Patent Infringement (D.N.J. Jun. 26, 2015).
*Reckitt Benckiser LLC* v. *Dr. Reddy's Laboratories, Inc. and Dr. Reddy's Laboratories, Ltd.*, Answer and Counterclaims of Dr. Reddy's Laboratories, Inc. and Dr. Reddy's Laboratories, Ltd. (D.N.J. Sep. 4, 2015).
*Reckitt Benckiser LLC* v. *Dr. Reddy's Laboratories, Inc. and Dr. Reddy's Laboratories, Ltd.*, Plaintiffs' Opposition to Motion for Judgment on the Pleadings (D.N.J. Sep. 18, 2015).
*Reckitt Benckiser LLC* v. *Dr. Reddy's Laboratories, Inc. and Dr. Reddy's Laboratories, Ltd.*, Reckitt's Reply to Dr. Reddy's Laboratories, Inc.'s and Dr. Reddy's Laboratories, LTD.'s Counterclaims (D.N.J. Sep. 28, 2015).
*Reckitt Benckiser LLC* v. *Dr. Reddy's Laboratories, Inc. and Dr. Reddy's Laboratories, Ltd.*, Dr. Reddy's Laboratories' Preliminary Invalidity Contentions (D.N.J. Oct. 21, 2015).
*Reckitt Benckiser LLC* v. *Dr. Reddy's Laboratories, Inc. and Dr. Reddy's Laboratories, Ltd.*, Reckitt's Opposition to Defendants' Motion for Judgment on the Pleadings (D.N.J. Oct. 23, 2015).
*Reckitt Benckiser LLC* v. *Dr. Reddy's Laboratories, Inc. and Dr. Reddy's Laboratories, Ltd.*, Reckitt's Preliminary Responses to Defendants' Invalidity Contentions (D.N.J. Dec. 7, 2015).
*Reckitt Benckiser LLC* v. *Amneal Pharmaceuticals LLC*, Docket Entries (D.N.J.), 2020.
*Reckitt Benckiser LLC* v. *Amneal Pharmaceuticals LLC*, Complaint for Patent Infringement (D.N.J. Mar. 26, 2015).
*Reckitt Benckiser LLC* v. *Amneal Pharmaceuticals LLC*, Ameanl Pharmaceuticals LLC's Answer, Affirmative Defenses, and Counterclaims (D.N.J. Jun. 15, 2015).
*Reckitt Benckiser LLC* v. *Amneal Pharmaceuticals LLC*, Reckitt Benckiser's Reply to Amneal Pharmaceuticals LLC's Counterclaims (D.N.J. Jul. 9, 2015).
*Reckitt Benckiser LLC* v. *Amneal Pharmaceuticals LLC*, Defendant Amneal Pharmaceuticals LLC's Rule 12(c) Motion for Judgment on the Pleadings to Plaintiff's Claims for Infringement (D.N.J. Aug. 14, 2015).
*Reckitt Benckiser LLC* v. *Amneal Pharmaceuticals LLC*, Amneal Pharmaceuticals LLC's Non-Infringement Contentions (D.N.J. Aug. 28, 2015).
*Reckitt Benckiser LLC* v. *Amneal Pharmaceuticals LLC*, Amneal Pharmaceuticals LLC's Invalidity Contentions (D.N.J. Aug. 28, 2015).

(56) References Cited

OTHER PUBLICATIONS

*Reckitt Benckiser LLC* v. *Amneal Pharmaceuticals LLC*, Plaintiff Reckitt Benckiser's Opposition to Defendant Amneal's Rule 12(c) Motion for Judgment on the Pleadings (D.N.J. Sep. 18, 2015).
*Reckitt Benckiser LLC* v. *Amneal Pharmaceuticals LLC*, Amneal Pharmaceuticals LLC's Answers to Plaintiff Reckitt Benckiser LLC's First Set of Interrogatories (Nos. 1-7) (D.N.J. Oct. 20, 2015).
*Reckitt Benckiser LLC* v. *Amneal Pharmaceuticals LLC*, Amneal Pharmaceuticals LLC's Supplemental Invalidity Contentions (D.N.J. Oct. 21, 2015).
*Reckitt Benckiser LLC* v. *Dr. Reddy's Laboratories, Ltd., et al., Reckitt Benckiser LLC* v. *Amneal Pharmaceuticals LLC, et al.*, Order Denying Judgment on the Pleadings (D.N.J. Jan. 15, 2016).
*Reckitt Benckiser LLC* v. *Amneal Pharmaceuticals LLC*, Stipulation of Dismissal of Claims, Defenses and Counterclaims for U.S. Pat. No. 6,372,252 (D.N.J. May 25, 2016).
*Reckitt Benckiser LLC* v. *Amneal Pharmaceuticals LLC*, Stipulation of Dismissal of Claims, Defenses and Counterclaims for U.S. Pat. Nos. 6,372,252 and 6,955,821 (D.N.J. May 25, 2016).
*Reckitt Benckiser LLC* v. *Amneal Pharmaceuticals LLC*, Reckitt's Opposition to Defendant's Motion for Summary Judgment of Non-Infringement (D.N.J. Jun. 17, 2016).
*Reckitt Benckiser LLC* v. *Amneal Pharmaceuticals LLC*, Supplemental Brief in Support of Defendants' Motion for Summary Judgment of Non-Infringement (D.N.J. Nov. 14, 2016).
*Reckitt Benckiser LLC* v. *Amneal Pharmaceuticals LLC, Reckitt Benckiser LLC* v. *Dr. Reddy's Laboratories, Ltd.*, Order Denying Defendant's Motion for Summary Judgment of Non-Infringement (D.N.J. Dec. 22, 2016).
*Reckitt Benckiser LLC* v. *Amneal Pharmaceuticals LLC, et al.*, Joint Claim Construction and Prehearing Statement (D.N.J. Jan. 12, 2017).
*Reckitt Benckiser LLC* v. *Amneal Pharmaceuticals LLC*, Defendants' Opening Claim Construction Brief (D.N.J. Feb. 2, 2017).
*Reckitt Benckiser LLC* v. *Amneal Pharmaceuticals LLC, et al.*, Expert Declaration of Dr. Martyn C. Davies (D.N.J. Feb. 23, 2017).
"Package Insert Emplate for Guaifenesin, Tablet/Capsule/Syrup", http://npra.moh.gov.my/images/reg-and-noti-/PI/non-poison/GuaiphenesinFINAL.pdf, (2013).
Angiolillo et al., "Clinical Pharmacology and Cardivascular Safety of Naproxen." Am. J. Cardiovasc. Drug, 17, pp. 97-107 (2017).
Barbara G. Wells et al., Pharmacotherapy Handbook, 691-6923 (8th ed. 2012).
"Empty Capsule Size Chart," https://www.capsuline.com/emptycapsule-size-chart/ (retrieved Nov. 17, 2016).
Mura et al., "Thermal Behavior and Dissolution Properties of Naproxen from Binary and Ternary Solid Dispersions," Drug Dev. Ind. Pharm., 25(3), 257-264 (1999).
*Reckitt Benckiser LLC* v. *Amneal Pharmaceuticals LLC, et al.*, Plaintiff Reckitt Benckiser's Responsive Markman Brief (D.N.J. Feb. 23, 2017).
*Reckitt Benckiser LLC* v. *Amneal Pharmaceuticals LLC, et al.*, Order Adopting Claim Construction (D.N.J. Mar. 30, 2017).
*Reckitt Benckiser LLC* v. *Dr. Reddy's Laboratories, Ltd., et al., Reckitt Benckiser LLC* v. *Amneal Pharmaceuticals LLC, et al.*, Final Judgment (D.N.J. Aug. 22, 2017).
*Reckitt Benckiser LLC* v. *Amneal Pharmaceuticals LLC*, Appeal Docket Entries (Fed. Cir.), 2020.
*Reckitt Benckiser LLC* v. *Amneal Pharmaceuticals LLC, Dr. Reddy's Laboratories, Inc., Dr. Reddy's Laboratories, Ltd.*, Non-Confidential Brief for Plaintiff (Fed. Cir. Dec. 20, 2017).
*Reckitt Benckiser LLC* v. *Amneal Pharmaceuticals LLC, Dr. Reddy's Laboratories, Inc., Dr. Reddy's Laboratories, Ltd.*, Brief for Defendants (Fed. Cir. Feb. 15, 2018).
*Reckitt Benckiser LLC* v. *Amneal Pharmaceuticals LLC, Dr. Reddy's Laboratories, Inc., Dr. Reddy's Laboratories, Ltd.*, Reply Brief for Plaintiff (Fed. Cir. Mar. 22, 2018).
*Reckitt Benckiser LLC* v. *Amneal Pharmaceuticals LLC, Dr. Reddy's Laboratories, Inc., Dr. Reddy's Laboratories, Ltd.*, Appeal Judgment (Fed. Cir. Sep. 10, 2018).
*Reckitt Benckiser LLC* v. *Dr. Reddy's Laboratories, Ltd., et al., Reckitt Benckiser LLC* v. *Amneal Pharmaceuticals LLC, et al.*, Public Opinion (D.N.J. Sep. 10, 2018).
*Reckitt Benckiser LLC* v. *Amneal Pharmaceuticals LLC*, Opinion (D.N.J. Oct. 25, 2019).
21 C.F.R. 341 Cold, cough, allergy, bronchodilator and antiasthmatic drug products for over-the-counter human use, Fed. Reg. vol. 54, No. 38 (1989).
Ansel, Howard C., "Introduction to Pharmaceutical Dosage Forms," Chapter 4 (8th ed. 1985).
Bodmeier, R., et al., "Prolonged release multiple unit dosage forms based on water soluble cellulosic polymers or aqueous latexes, Proceedings 18th International Symposium on controlled Release of Bioactive Materials" (1991).
Bodmeier, Roland et al., "Microencapsulation of drugs with aqueous colloidal polymer," J. Pharm. Sci., vol. 82, No. 2, 191-194 (1993).
Brock, Michael H. et al., "Use of In Vitro and In Vivo Data in the Design, Development, and Quality Control of Sustained-Release Decongestant Dosage Forms," 14 (4) 430-437 (1994).
Chai, Chih-Kun Pauline, "Determination of dextrorphan and guaifenesin by high performance liquid chromatography—pharmacokinetics of guaifenesin" (1994).
Davis, S. S. et al., "Transit of pharmaceutical dosage forms through the small intestine," http://gut.bmj.com/ (Aug. 22, 2016).
Dr. Crooks Second Declaration ('252 Re-Exam) (Aug. 21, 2006).
European Search Report issued in European Patent Application No. 16 785 649.1, dated Apr. 30, 2019.
FDA approved labeling for Mucinex® at ART0009679-86, 2002.
Ford, James L., "Design and Evaluation of Hydroxypropyl Methylcellulose Matrix Tablets for Oral Controlled Release: A Historical Perspective," American Association of Pharmaceutical Scientists (2014).
Gennaro, Alfonso R., "Remington: The Science and Practice of Pharmacy," 20th Ed. Ch. 53, 2000.
Gennaro, Alfonso R., "Remington: The Science and Practice of Pharmacy," Ch. 10, 36, 91 (18th ed., 1990).
Guaifenesin, Drug Bank https://www.drugbank.ca/drugs/DB00874 (Mar. 16, 2017).
Gudipati, Manga Raju, "In vitro/in vivo correlation approach for the development of drug delivery systems," (1990).
Haan, P. De, et al., "Oral Controlled Release Dosage Forms. A review," Pharmaceutisch Weekblad Scientific Edition, vol. 6 (1984).
Huber, et al., Journal of Pharmaceutical Sciences vol. 55, pp. 974-997 (1966).
Kim, C., "Controlled Release Dosage Form Design," Technomic Publishing Co.,Inc. (2000).
Klancar, Uros et al., "Determining the Polymer Threshold Amount for Achieving Robust Drug Release from HPMC and HPC Matrix Tablets Containing a High-Dose BCS Class I Model Drug: In Vitro and In Vivo Studies," American Association of Pharmaceutical Scientists (2015).
Lee, Peter I.D., et al., "Pharmacokinetic Analysis" Ch. 8 (1996).
Lipinski, Christopher A. et al., "Experimental and computational approaches to estimate solubility and permeability in drug discovery and development settings," Advanced Drug Delivery Reviews 46 3-26 (2001).
Melegari, Cecilia et al., "Ethylcellulose film coating of guaifenesin-loaded pellets: A comprehensive evaluation of the manufacturing process to prevent drug migration," European Journal of Pharmaceutics and Biopharmaceutics 100 15-26 (2016).
Pade, Vaishali, et al., "Bioavailability of pseudoephedrine from controlled release formulation in the presence of guaifensin in human volunteers, Biopharmaceutics & Drug Disposition," vol. 16, 381-391 (1995).
Physicians' Desk Reference to Pharmaceutical Specialties and Biologicals 3202 (53rd ed. 1999).
Rollins, Douglas E., "Clinical Pharmacokinetics" Ch. 59.
Sharmin, Nahid et al., "A Novel Method to Study the Effect of pH and Excipients on Water Uptake and Swelling Behaviour of Carbopol Polymers," Bangladesh Pharmaceutical Journal vol. 13, No. 2 (Jul. 2010).

(56) References Cited

OTHER PUBLICATIONS

The Merck Index, 13th ed. (2001), at p. 812, Appendix C of '252 Reexam, Aug. 21, 2006 Amendment.
Thompson, Gary A. et al., "Guaifensin Pharmacokinetics Following Single-Dose Oral Administration in Children Aged 2 to 17 Years," The Journal of Clinical Pharmacology 56(7) 894-901 (2016).
U.S. Department of Health and Human Services, Food and Drug Administration, Center for Drug Evaluation and Research (CDER), Guidance for Industry, "Bioavailability and Bioequivalence Studies for Orally Administered Drug Products—General Considerations" (Mar. 2003).
U.S. Department of Health and Human Services, Food and Drug Administration, Center for Drug Evaluation and Research (CDER), Guidance for Industry, "Bioavailability and Bioequivalence Studies Submitted in NDAs or INDs—General Considerations," (Mar. 2014).
Velasco, M. Victoria et al., "Influence of drug: hydroxypropylmethylcellulose ratio, drug and polymer particle size and compression force on the release of diclofenac sodium from HPMC tablets," Journal of Controlled Release 57 75-85 (1999).
*Reckitt Benckiser LLC v. Aurobindo Pharma Limited et al.*, Docket Entries (D. Del.), 2014.
*Reckitt Benckiser LLC v. Aurobindo Pharma Limited et al.*, Complaint (D. Del. Sep. 17, 2014).
*Reckitt Benckiser LLC v. Aurobindo Pharma Limited et al.*, Answer, Defenses and Counterclaims of Aurobindo Pharma Limited and Aurobindo Pharma USA, Inc. (D. Del. Nov. 17, 2014).
*Reckitt Benckiser LLC v. Aurobindo Pharma Limited et al.*, Reckitt Benckiser's Reply to Aurobindo Pharma Limited and Aurobindo Pharma USA, Inc.'s Counterclaims (D. Del. Dec. 11, 2014).
*Reckitt Benckiser LLC v. Aurobindo Pharma Limited et al.*, Plaintiff Reckitt Benckiser's Opening Claim Construction Brief (D. Del. Mar. 4, 2016).
*Reckitt Benckiser LLC v. Aurobindo Pharma Limited et al.*, Aurobindo Pharma Limited and Aurobindo Pharma USA, Inc.'s Opening Claim Construction Brief (D. Del. Mar. 10, 2016).
*Reckitt Benckiser LLC v. Aurobindo Pharma Limited et al.*, Aurobindo Pharma Limited and Aurobindo Pharma USA, Inc.'s Responsive Claim Construction Brief (D. Del. Mar. 29, 2016).
*Reckitt Benckiser LLC v. Aurobindo Pharma Limited et al.*, Declaration of Michael F. Nullet (D. Del. Mar. 29, 2016).
*Reckitt Benckiser LLC v. Aurobindo Pharma Limited et al.*, Plaintiff Reckitt Benckiser's Responsive Claim Construction Brief (D. Del. Mar. 29, 2016).
*Reckitt Benckiser LLC v. Aurobindo Pharma Limited et al.*, Order for Partial Dismissal of Claims (D. Del. Aug. 24, 2016).
*Reckitt Benckiser LLC v. Aurobindo Pharma Limited et al.*, Memorandum Opinion (D. Del. Nov. 3, 2016).
*Reckitt Benckiser LLC v. Aurobindo Pharma Limited et al.*, Order (D. Del. Nov. 3, 2016).
*Reckitt Benckiser LLC v. Aurobindo Pharma Limited et al.*, Oral Order (D. Del. Dec. 21, 2016).
*Reckitt Benckiser LLC v. Aurobindo Pharma Limited et al.*, Aurobindo Pharma Limited and Aurobindo Pharma USA, Inc.'s Brief in Support of its Motion for Summary Judgment (D. Del. Dec. 29, 2016).
*Reckitt Benckiser LLC v. Aurobindo Pharma Limited et al.*, Plaintiff Reckitt Benckiser LLC's Answering Brief in Opposition to Defendants' Motion for Summary Judgment (D. Del. Jan. 24, 2017).
*Reckitt Benckiser LLC v. Aurobindo Pharma Limited et al.*, Aurobindo Pharma Limited and Aurobindo Pharma USA, Inc.'s Reply in Support of its Motion for Summary Judgment ( (D. Del. Jan. 31, 2017).
*Reckitt Benckiser LLC v. Aurobindo Pharma Limited et al.*, Memorandum Opinion (D. Del. Mar. 6, 2017).
*Reckitt Benckiser LLC v. Aurobindo Pharma Limited et al.*, Order (D. Del. Mar. 6, 2017).
*Reckitt Benckiser LLC v. Aurobindo Pharma Limited et al.*, Final Judgment Order (D. Del. Mar. 13, 2017).

European Examination Report issued Jul. 19, 2019, in counterpart application EP 15791011.8 (3 pages).
Physicians' Desk Reference to Pharmaceutical Specialties and Biologicals, passim (46th ed. 1992) PGFSN 054207-054265.
Physicians' Desk Reference to Pharmaceutical Specialties and Biologicals, passim (50th ed. 1996) PGFSN 054266-054360.
Physicians' Desk Reference to Pharmaceutical Specialties and Biologicals, passim (51st ed. 1997) PGFSN 054361-054442.
Physicians' Desk Reference to Pharmaceutical Specialties and Biologicals, passim (52d ed. 1998) PGFSN 054443-054508.
Physicians' Desk Reference to Pharmaceutical Specialties and Biologicals, passim (53d ed. 1999) PGFSN 054509-054572.
Random House Unabridged Dictionary 1780 (2d ed. 1993).
Textbook of Therapeutics: Drug and Disease Management 1255 (Eric T. Herfindal & Dick R. Gourley eds., 6th ed. 1996) PGFSN 054880-054882.
The United States Pharmacopeia / The National Formulary 19-20, 724-725 (USP 23 / NF 18 1995) PGFSN 054594-054599.
Webster's New World/Stedman's Concise Medical Dictionary 345 (1987).
Wilson and Gisvold's Textbook of Organic Medicinal and Pharmaceutical Chemistry 948-956 (John H. Block & John M. Beale, Jr. eds., 11th ed. 2004) PGFSN 054738-054748.
The Dow Chemical Company, Formulating Sustained Release Pharmaceutical Products With Methocel (1982).
Thomson Reuters Press Release, "Thomson Healthcare Launches PDRhealth.com" pp. 1-3 (Nov. 5, 2007) (found at http://thomsonreuters.com/content/press_room/tsh/mdx_ThomHcareLaunchesPDRhealth on Mar. 31, 2010).
47 FR 30002-30010 (Jul. 9, 1982) PGFSN 053860-053880.
54 FR 8494-8509 (Feb. 28, 1989) ART 0489984-0489999 & PGFSN 053881-053916.
Food and Drug Administration, Compliance Program Guidance Manual, Program 7361.003, Chapter 61—OTC Drug Evaluation (May 2007).
Food and Drug Administration, Inspections, Compliance, Enforcement, and Criminal Investigations, CPG Sec. 450.200 Drugs—General Provisions and Administrative Procedures for Recognition as Safe and Effective (CPG 7132b.15) (found at fda.gov/ICECI/.../ ucm074388.htm on Oct. 15, 2009).
U.S. Department of Health and Human Services, Food and Drug Administration, Center for Devices and Radiological Health, Guidance for Industry and FDA Staff, "Format for Traditional and Abbreviated 510(k)s" (Aug. 12, 2005).
U.S. Department of Health and Human Services, Food and Drug Administration, Center for Drug Evaluation and Research (CDER), Guidance for Industry, "Extended Release Oral Dosage Forms: Development, Evaluation, and Applications of In Vitro/In Vivo Correlations" (Sep. 1997).
U.S. Department of Health and Human Services, Food and Drug Administration, Center for Drug Evaluation and Research (CDER), Guidance for Industry, "SUPAC-MR: Modified Release Solid Oral Dosage Forms, Scale-Up and Postapproval Changes: Chemistry, Manufacturing, and Controls; In Vitro Dissolution Testing and In Vivo Bioequivalence Documentation" (Sep. 1997).
U.S. Department of Health and Human Services, Food and Drug Administration, Center for Drug Evaluation and Research (CDER), Guidance for Industry, "Waiver of In Vivo Bioavailability and Bioequivalence Studies for Immediate Release Solid Oral Dosage Forms Containing Certain Active Moieties/Active Ingredients Based on a Biopharmaceutics Classification System," Draft Guidance (Jan. 1999) PGFSN 054706-054719.
U.S. Department of Health and Human Services, Food and Drug Administration, Center for Drug Evaluation and Research (CDER), Guidance for Industry, "Statistical Approaches to Establishing Bioequivalence" (Jan. 2001).
U.S. Department of Health and Human Services, Food and Drug Administration, Center for Drug Evaluation and Research (CDER), Guidance for Industry, "Food-Effect Bioavailability and Fed Bioequivalence Studies" (Dec. 2002).
U.S. Department of Health and Human Services, Food and Drug Administration, Center for Drug Evaluation and Research (CDER),

(56) References Cited

OTHER PUBLICATIONS

Guidance for Industry, "Power Blends and Finished Dosage Units—Stratified In-Process Dosage, Unit Sampling and Assessment," Draft Guidance (Oct. 2003).
U.S. Department of Health and Human Services, Food and Drug Administration, Center for Drug Evaluation and Research (CDER), Guidance for FDA Staff and Industry, "Marketed Unapproved Drugs—Compliance Policy Guide, Sec. 440.100 Marketed New Drugs Without Approved NDAs or ANDAs" (Jun. 2006).
Correspondence from David J. Horowitz, Esq., Director, Office of Compliance, Center for Drug Evaluation and Research, Food and Drug Administration to 45 entities, Guaifenesin single product Warning Letters (Oct. 11, 2002).
Correspondence from David J. Horowitz, Esq., Director, Office of Compliance, Center for Drug Evaluation and Research, Food and Drug Administration to 26 entities, Guaifenesin multiple products Warning Letters (Oct. 11, 2002).
Correspondence from Salomon Stavchansky Ph.D., Professor of Pharmaceutics and Alcon Centennial Professor of Pharmacy to R. Andrew Morgan, R.Ph., Adams Laboratories, Inc., Regulatory Affairs, including attachment (Feb. 1, 1994) ART 0447100-0447152.
STN Search Report 1-5 (Oct. 7, 2009).
Drituss G and Q-Bid LA, Qualitest 011.
Q-Bid LA labels, Qualitest 015 & 017.
Drituss G and Q-Bid LA and labels, Vintage 011-018.
*Adams Respiratory Therapeutics, Inc., et al. v. Perrigo Company, et al.*, Plaintiffs' Opening Memorandum of Law on Claim Construction (W.D. Mich. May 21, 2009).
*Adams Respiratory Therapeutics, Inc., et al. v. Perrigo Company, et al.*, Declaration of Dr. Thomas Foster (W.D. Mich. May 21, 2009).
*Adams Respiratory Therapeutics, Inc., et al. v. Perrigo Company, et al.*, Defendants' Markman Brief In Support of Their Proposed Claim Construction (W.D. Mich. May 21, 2009).
*Adams Respiratory Therapeutics, Inc., et al. v. Perrigo Company, et al.*, Declaration of Walter G. Chambliss, Ph.D. (W.D. Mich. May 20, 2009).
*Adams Respiratory Therapeutics, Inc., et al. v. Perrigo Company, et al.*, Plaintiffs' Responsive Memorandum of Law on Claim Construction (W.D. Mich. Jun. 22, 2009).
*Adams Respiratory Therapeutics, Inc., et al. v. Perrigo Company, et al.*, Supplemental Declaration of Dr. Thomas Foster (W.D. Mich. Jun. 22, 2009).
*Adams Respiratory Therapeutics, Inc., et al. v. Perrigo Company, et al.*, Defendants' Responsive Brief to Plaintiffs' Opening Memorandum of Law on Claim Construction (W.D. Mich. Jun. 22, 2009).
*Adams Respiratory Therapeutics, Inc., et al. v. Perrigo Company, et al.*, Plaintiffs' Reply Memorandum of Law on Claim Construction (W.D. Mich. Jul. 8, 2009).
*Adams Respiratory Therapeutics, Inc., et al. v. Perrigo Company, et al.*, Second Supplemental Declaration of Dr. Thomas Foster (W.D. Mich. Jul. 8, 2009).
*Adams Respiratory Therapeutics, Inc., et al. v. Perrigo Company, et al.*, Defendants' Reply In Support of Defendants' Markman Brief In Support of Their Proposed Claim Construction (W.D. Mich. Jul. 8, 2009).
*Adams Respiratory Therapeutics, Inc., et al. v. Perrigo Company, et al.*, Supplemental Declaration of Walter G. Chambliss, Ph.D. (W.D. Mich. Jul. 7, 2009).
*Adams Respiratory Therapeutics, Inc., et al. v. Perrigo Company, et al.*, Order and Proposed Construction of Disputed Terms (W.D. Mich. Jul. 24, 2009).
*Adams Respiratory Therapeutics, Inc., et al. v. Perrigo Company, et al.*, Submission In Response to The Court's Proposed Construction of Disputed Terms (W.D. Mich. Aug. 7, 2009).
*Adams Respiratory Therapeutics, Inc., et al. v. Perrigo Company, et al.*, Defendants' Response to The Court's Jul. 24, 2009 Proposed Construction of Disputed Terms (W.D. Mich. Aug. 7, 2009).
*Adams Respiratory Therapeutics, Inc., et al. v. Perrigo Company, et al.*, Order Adopting Proposed Claim Construction (W.D. Mich. Aug. 24, 2009).
*Adams Respiratory Therapeutics, Inc., et al. v. Perrigo Company, et al.*, Memorandum In Support of Plaintiffs' Motion for Reconsideration of Court's Aug. 24, 2009 Order Regarding Claim Construction of The Term "Fully Bioavailable In The Subject's Stomach"—Redacted (W.D. Mich. Dec. 4, 2009).
*Adams Respiratory Therapeutics, Inc., et al. v. Perrigo Company, et al.*, Defendants' Opposition to Plaintiffs' Motion for Reconsideration of The Court's Aug. 24, 2009 Order Construing The Term "Fully Bioavailable In The Subject's Stomach"—Redacted (W.D. Mich. Dec. 14, 2009).
*Adams Respiratory Therapeutics, Inc., et al. v. Perrigo Company, et al.*, Defendants' Memorandum In Support of Their Motion for Summary Judgment of Non-Infringement—Redacted (W.D. Mich. Nov. 16, 2009).
*Adams Respiratory Therapeutics, Inc., et al. v. Perrigo Company, et al.*, Plaintiffs' Memorandum of Law In Opposition to Defendants' Motion for Summary Judgment of Non-Infringement—Redacted (W.D. Mich. Dec. 14, 2009).
A. S. Hussain et al., "The Biopharmaceutics Classification System: Highlights of the FDA's Draft Guidance," Dissolution Technologies May 1999 Article #1, pp. 1-4 and Biopharmaceutics Classification Figures 1-3, pp. 1-2 (found at http://www.dissolutiontech.com/DTresour/599articles/Biopharm_Class2_copy.html and http://www.dissolutiontech.com/DTresour/599articles/BiopharmFig1-3.html on Oct. 15, 2009).
L. Kalantzi et al., "Biowaiver Monographs for Immediate Release Solid Oral Dosage Forms: Acetaminophen (Paracetamol)," J. Pharm. Sciences 95(1):4-14 (2006).
Lydia C. Kaus et al., "The Effect of In Vivo Dissolution, Gastric Emptying Rate, and Intestinal Transit Time on the Peak Concentration and Area-Under-the Curve of Drugs with Different Gastrointestinal Permeabilities," Pharm. Research 16(2):272-280 (1999).
TH. Knapp, "Der Einfluss von Guajakolderivaten auf die Ausscheidung der Glukuronsäure," J. Suisse de Chimie et Pharmacie LX(17):229-231, 245-248, 257-262 (1911), with certified translation.
Leszek Krowczynski, Extended-Release Dosage Forms 4-6, 51-58 (Dorota Porebska Brozyna trans. 1987).
C. Gordon Law, "Dose Proportionality," in Encyclopedia of Biopharmaceutical Statistics 295-297 (Shein-Chung Chow ed., 2d ed., revised and expanded, 2003).
Mark A. Longer & Joseph R. Robinson, "Sustained-Release Delivery Systems," in Remington's Pharmaceutical Sciences 1644-1661 (Alfonso R. Gennaro ed., 17th ed. 1985).
Carol N. Manners et al., "Distribution Coefficient, a Convenient Term for the Relation of Predictable Physico-Chemical Properties to Metabolic Processes," Xenobiotica 18(3):331-350 (1988) PGFSN 054769-054790.
Marilyn N. Martinez & Gordon L. Amidon, "A Mechanistic Approach to Understanding the Factors Affecting Drug Absorption: A Review of Fundamentals," J. Clin. Pharmacol. 42:620-643 (2002).
William R. Maynard, Jr. & Robert B. Bruce, "GLC Determination of Guaiacol Glyceryl Ether in Blood," J. Pharm. Sciences 59(9):1346-1348 (1970) PGFSN 054808-054811.
Hussain Y. Mohammed & Frederick F. Cantwell, "Liquid Chromatographic Analysis of Pharmaceutical Syrups Using Pre-Columns and Salt-Adsorption on Amberlite XAD-2," Analytical Chemistry 50(3):491-496 (1978) PFGSN 054812-054817.
Sakae Obara et al, "Evaluation of Several Grades of Hydroxypropyl Methylcellulose for Use in a Sustained-Release Tablet Matrix," Advances in Pharmaceutics and Pharm. Tech., pp. 212-219 (1989).
Rebecca L. Oberle & Gordon L. Amidon, "The Influence of Variable Gastric Emptying and Intestinal Transit Rates on the Plasma Level Curve of Cimetidine; An Explanation for the Double Peak Phenomenon," J. Pharmacokinetics & Biopharmaceutics 15(5):529-544 (1987).
Eugene L. Parrott, "Solid Dosage Forms," in Prescription Pharmacy, Dosage Formulation and Pharmaceutical Adjuncts 103-162 (Joseph B. Sprowls, Jr. ed., 2d ed. 1970) PGFSN 053056-053116.
James E. Polli et al., "Summary Workshop Report: Biopharmaceutics Classification System-Implementation Challenges and Extension Opportunities," J. Pharm. Sciences 93(6):1375-1381 (2004).
W. Steven Pray, Nonprescription Product Therapeutics 225-231 (1999).

(56) References Cited

OTHER PUBLICATIONS

Gurvinder Singh Rekhi et al., "Identification of Critical Formulation and Processing Variables for Metoprolol Tartrate Extended-Release (ER) Matrix Tablets," J. Controlled Release 59:327-342 (1999).

Manford Robinson et al., "Sustained Action Dosage Forms," in The Theory and Practice of Industrial Pharmacy 439-465 (Leon Lachman et al. eds., 2d ed. 1976) PGFSN 053001-053029.

P. E. Rolan, "The Assessment of Pharmacokinetics in Early Phase Drug Evaluation," in Handbook of Phase I/II Clinical Drug Trials 169-175 (John O'Grady & Pieter H. Joubert eds. 1997).

Earl Rosen & Joseph V. Swintosky, "Preparation of a 35S Labelled Trimeprazine Tartrate Sustained Action Product for Its Evaluation in Man," J. of Pharmacy and Pharmacology, XII Supp.:237T-244T (1960) PGFSN 052992-053000.

Edward M. Rudnic & Mary Kathryn Kottke, "Tablet Dosage Forms," in Modern Pharmaceutics 333, 359-364 (Gilbert S. Banker & Christopher T. Rhodes eds., 3d ed., revised and expanded, 1996).

H. Rupprecht & D. Regensburg, "XIV. Silicium Dioxide and Silicates in Drug Delivery," in Controlled Drug Delivery 197-225 (Bernd W. Müller ed. 1987).

Leroy A. Shervington & Amal Shervington, "Guaifenesin," in Analytical Profiles of Drug Substances and Excipients 121-164 (Harry G. Brittain ed. 1998) PGFSN 054626-054671.

Patrick J. Sinko & Gordon L. Amidon, "Characterization of the Oral Absorption of β-Lactam Antibiotics. I. Cephalosporins: Determination of Intrinsic Membrane Absorption Parameters in the Rat Intestine In Situ," Pharm. Research 5(10) 645-650 (1988).

J. P. Skelly et al., "Scaleup of Oral Extended-Release Dosage Forms," Pharm. Research 10(12):1800-1805 (1993).

Dennis Smith et al., "Design of Drugs Involving the Concepts and Theories of Drug Metabolism and Pharmacokinetics," Medicinal Research Reviews 16(3):243-266 (1996) PGFSN 054600-054625.

Dennis Smith, "Can We Design Drugs with Low Variability," in Variability in Human Drug Response 251-261 (G.T. Tucker ed. 1999) PGFSN 054727-054737.

Dennis Smith & Barry Jones, "Variability in Drug Response as a Factor in Drug Design," Current Opinion in Drug Discovery & Development 2(1):33-41 (1999) PGFSN 054672-054681.

Joel T. Smith & Dutt V. Vinjamoori, "Rapid Determination of Logarithmic Partition Coefficients Between n-Octanol and Water Using Micellar Electrokinetic Capillary Chromatography," J. Chromatography B: Biomed. Applications 669(1):59-66 (1995) PGFSN 054759-054768.

David O. Thueson, Thueson's Guide to Over-The-Counter Drugs 54-57 (1995).

Klara Valkó et al., "Chromatographic Hydrophobicity Index by Fast-Gradient RP-HPLC: A High-Throughput Alternative to log P/log D," Anal. Chem. 69:2022-2029 (1997).

Daniel L. Wagner & Vikram S. Patel, "Steady-State Human Pharmacokinetics and Bioavailability of Guaifenesin and Pseudoephedrine in a Sustained-Release Tablet Relative to Immediate-Release Liquids," Int'l J. Pharmaceutics 114:171-176 (1995) PGFSN 053117-053122.

Zheng Wang et al., "In-Vivo and In-Vitro Evaluations of a Modified-Release Oral Dosage Form of Nifedipine by Hybridization of Hydroxypropyl-β-Cyclodextrin and Hydroxypropylcelluloses in Dogs," J. Pharm. Pharmacol. 46:505-507 (1994) PGFSN 052869-52871.

Hong Gi Yi et al., "Formulation of a Extended Release Tablet Containing Dexibuprofen," Arch. Pharm. Res. 31(12):1637-1643 (2008).

Lawrence X. Yu & Gordon L. Amidon, "A Compartmental Absorption and Transit Model for Estimating Oral Drug Absorption," Int'l J. Pharmaceutics 186:119-125 (1999).

Excipients and Delivery Systems for Pharmaceutical Formulations 123-124, 186-190 (D. R. Karsa & R. A. Stephenson eds. 1995).

Handbook of Pharmaceutical Excipients 252-261, 280-282, 424-427 (Ainley Wade & Paul J. Weller eds., 2d ed. 1994).

Handbook of Pharmaceutical Excipients 188-191 (Raymond C. Rowe et al. eds., 5th ed. 2006).

The Merck Index 716-717 (Susan Budavari et al. eds., 11th ed. 1989) PGFSN 054754-054758.

The Merck Index 776-777 (Susan Budavari et al. eds., 12th ed. 1996) PGFSN 054749-054753.

Pharmaceutical Dosage Forms, vol. 1, pp. 2, 241, 247-284 (Herbert A. Lieberman et al. eds., 2d ed., revised and expanded, 1989).

Pharmaceutical Dosage Forms, vol. 2, pp. 7-11, 13-20, 60-67 (Herbert A. Lieberman et al. eds., 2d ed., revised and expanded, 1990).

Physicians' Desk Reference to Pharmaceutical Specialties and Biologicals 216, 490-491 (5th ed. 1951) PGFSN 053917-053921.

Physicians' Desk Reference to Pharmaceutical Specialties and Biologicals 248, 517, 522, 570 (9th ed. 1955) PGFSN 053922-053927.

Physicians' Desk Reference to Pharmaceutical Specialties and Biologicals, passim (14th ed. 1960) PGFSN 053928-053941.

Physicians' Desk Reference to Pharmaceutical Specialties and Biologicals, passim (25th ed. 1971) PGFSN 053942-053983.

Physicians' Desk Reference to Pharmaceutical Specialties and Biologicals, passim (34th ed. 1980) PGFSN 053984-054044.

Physicians' Desk Reference to Pharmaceutical Specialties and Biologicals, passim (39th ed. 1985) PGFSN 054045-054130.

Physicians' Desk Reference to Pharmaceutical Specialties and Biologicals, passim (40th ed. 1986) PGFSN 054131-054206.

*Adams Respiratory Therapeutics, Inc., et al. v. Perrigo Company, et al.*, Defendants' First Supplemental Responses and Objections to Adams' Second Set of Interrogatories (Nos. 13-14) (W.D. Mich. Jun. 30, 2009).

*Adams Respiratory Therapeutics, Inc., et al. v. Perrigo Company, et al.*, Expert Report of Walter G. Chambliss—Redacted (W.D. Mich. Aug. 10, 2009).

*Adams Respiratory Therapeutics, Inc., et al. v. Perrigo Company, et al.*, Rule 26 Expert Report of John T. Goolkasian, Esq. (W.D. Mich. Aug. 4, 2009).

*Adams Respiratory Therapeutics, Inc., et al. v. Perrigo Company, et al.*, Expert Report of Michael Mayersohn, Ph.D. (W.D. Mich. Aug. 7, 2009).

*Adams Respiratory Therapeutics, Inc., et al. v. Perrigo Company, et al.*, Responsive Expert Report of Dr. Gordon Amidon—Redacted (W.D. Mich. Sep. 18, 2009).

*Adams Respiratory Therapeutics, Inc., et al. v. Perrigo Company, et al.*, Responsive Expert Report of Dr. Thomas S. Foster—Redacted (W.D. Mich. Sep. 18, 2009).

*Adams Respiratory Therapeutics, Inc., et al. v. Perrigo Company, et al.*, Expert Report of Charles E. Van Horn (W.D. Mich. Sep. 18, 2009).

*Adams Respiratory Therapeutics, Inc., et al. v. Perrigo Company, et al.*, Reply Expert Report of Walter G. Chambliss, Ph.D.—Redacted (W.D. Mich. Oct. 9, 2009).

*Adams Respiratory Therapeutics, Inc., et al. v. Perrigo Company, et al.*, Reply Expert Report of John T. Goolkasian, Esq. (W.D. Mich. Oct. 7, 2009).

*Adams Respiratory Therapeutics, Inc., et al. v. Perrigo Company, et al.*, Reply Expert Report of Michael Mayersohn, Ph.D.—Redacted (W.D. Mich. Oct. 8, 2009).

*Adams Respiratory Therapeutics, Inc., et al. v. Perrigo Company, et al.*, Supplemental Expert Report of Dr. Gordon Amidon—Redacted (W.D. Mich. Nov. 14, 2009).

*Adams Respiratory Therapeutics, Inc., et al. v. Perrigo Company, et al.*, Second Supplemental Expert Report of Dr. Gordon Amidon—Redacted (W.D. Mich. Nov. 15, 2009).

J.B. Aluri & S. Stavchansky, "Determination of Guaifenesin in Human Plasma by Liquid Chromatography in the Presence of Pseudoephedrine," J. of Pharm. & Biomed. Analysis 11(9):803-808 (1993) PGFSN 053048-053055.

Gordon L. Amidon et al., "Estimating Human Oral Fraction Dose Absorbed: A Correlation Using Rat Intestinal Membrane Permeability for Passive and Carrier-Mediated Compounds," Pharm. Research 5(10):651-654 (1988).

Gordon L. Amidon et al., "Effects of Gravity on Gastric Emptying, Intestinal Transit, and Drug Absorption," J. Clin. Pharmacol. 31:968-973 (1991).

(56) References Cited

OTHER PUBLICATIONS

Gordon L. Amidon et al., "A Theoretical Basis for a Biopharmaceutic Drug Classification: The Correlation of in Vitro Drug Product Dissolution and in Vivo Bioavailability," Pharm. Research 12(3):413-420 (1995).
Howard C. Ansel et al., Pharmaceutical Dosage Forms and Drug Delivery Systems 213-225 (6th ed. 1995).
Howard C. Ansel et al., Pharmaceutical Dosage Forms and Drug Delivery Systems 229-243 (7th ed. 1999).
A. Arancibia et al., "Pharmacokinetics and Bioavailability of a Controlled Release Amoxicillin Formulation," Int'l J. of Clin. Pharmacol., Therapy and Toxicology 25(2):97-100 (1987).
B. Huet De Barochez et al., "Influence of Drug Solubility in the Formulation of Hydrophilic Matrices," Drug Development and Industrial Pharmacy 15(14-16):2197-2212 (1989).
Joeby Bass et al., "An Evaluation of the Effect of Food on the Oral Bioavailability of Sustained-Release Morphine Sulfate Tablets (ORAMORPH SR) After Multiple Doses," J. Clin. Pharmacol. 32(11):1003-1007 (1992).
Henning H. Blume & Barbara S. Schug, "The Biopharmaceutics Classification System (BCS): Class III Drugs—Better Candidates for BA/BE Waiver?" European J. Pharm. Sciences 9:117-121 (1999) PGFSN 054720-054726.
Rudolph H. Blythe, "The Formulation and Evaluation of Sustained Release Products," Drug Standards 26(1):1-7 (1958) PGFSN 053162-053170.
Gerald W. Bottenfield et al., "Safety and Tolerability of a New Formulation (90mg/kg/day Divided Every 12 h) of Amoxicillin/Clavulanate (Augmentin®) in the Empiric Treatment of Pediatric Acute Otitis Media Caused by Drug-Resistant *Streptococcus pneumoniae*," Pediatr. Infect. Dis. J. 17(10):963-968 (1998).
Harold G. Boxenbaum, "Physiological and Pharmacokinetic Factors Affecting Performance of Sustained Release Dosage Forms," Drug Dev. & Industrial Pharmacy 8(1):1-25 (1982).
David E. Bugay & W. Paul Findlay, Pharmaceutical Excipients 289 (1999).
Xianhua Cao et al., "Permeability Dominates in Vivo Intestinal Absorption of P-gp Substrate with High Solubility and High Permeability," Molecular Pharmaceutics 2(4):329-340 (2005).
Rong-Kun Chang & Joseph R. Robinson, "Sustained Drug Release from Tablets and Particles Through Coating," in Pharmaceutical Dosage Forms, vol. 3, pp. 199-302 (Herbert A. Lieberman et al. eds., 2d ed., revised and expanded, 1990).
Jun Chen et al., "Superporous Hydrogels as a Platform for Oral Controlled Drug Delivery," in Handbook of Pharmaceutical Controlled Release Technology 211-224 (Donald L. Wise et al. eds. 2000).
Charles S. L. Chiao & Joseph R. Robinson, "Sustained-Release Drug Delivery Systems," in Remington: The Science and Practice of Pharmacy 1660-1675 (Alfonso R. Gennaro ed., 19th ed. 1995).
Yie W. Chien, Novel Drug Delivery Systems 747-776 (2d ed., revised and expanded, 1992).
Ferenc Csizmadia et al., "Prediction of Distribution Coefficient from Structure. 1. Estimation Model," J. Pharm. Sciences 86(7):865-871 (1997).
S. S. Davis et al., "Transit of Pharmaceutical Dosage Forms Through the Small Intestine," Gut 27:886-892 (1986).
J.G. Devane et al., "Pharmacokinetic and In-Vitro Characteristics of Sustained Release Verapamil Products," Drug Development and Industrial Pharmacy 16(7):1233-1248 (1990).
John Devane, "Oral Drug Delivery Technology: Addressing the Solubility/Permeability Paradigm," Pharm. Tech. 22(11):68-80 (1998).
John G. Devane & John G. Kelly, "Effect of Food on the Bioavailability of a Multiparticulate Sustained-Release Verapamil Formulation," Advances in Therapy 8(1):48-53 (1991).
M. R. Dobrinska & P. G. Welling, "Blood Levels from a Sustained-Release Dosage Form," J. Pharm. Sciences 17(10):1728-1729 (1998).
J.B. Dressman et al., "Physichemical Model for Dose-Dependent Drug Absorption," J. Pharm. Sciences 73(9):1274-1279 (1984).
J.B. Dressman et al., "Absorption Potential: Estimating the Fraction Absorbed for Orally Administered Compounds," J. Pharm. Sciences 74(5):588-589 (1985).
Natalie D. Eddington et al., "Development and Internal Validation of an In Vitro-In Vivo Correlation for a Hydrophilic Metoprolol Tartrate Extended Release Tablet Formulation," Pharm. Research 15(3):466-473 (1998).
M. El-Khawas et al., "Phenylpropanolamine Controlled-Release Tablets," Pharm. Ind. 55(4):392-395 (1993) PGFSN 052986-052991.
Mark G. Eller & Andrew A. Della-Coletta, "Absence of Effect of Food on Alprazolam Absorption from Sustained Release Tablets," Biopharmaceutics & Drug Disposition 11:31-37 (1990).
David Fleisher et al., "Drug, Meal and Formulation Interactions Influencing Drug Absorption After Oral Administration," Clin. Pharmacokinetics 36(3):233-254 (1999) PGFSN 05682-054705.
Arthur C. Guyton & John E. Hall, Textbook of Medical Physiology 793-802, 833-844 (9th ed. 1996).
Lester I. Harrison, "Kinetics of Absorption of a new Once-a-Day Formulation of Theophylline in the Presence and Absence of Food," J. Pharm. Sciences 82(6):644-648 (1993).
A.K. Hilton & P.B. Deasy, "In Vitro and In Vivo Evaluation of an Oral Sustained-Release Floating Dosage Form of Amoxycillin Trihydrate," Int'l J. Pharmaceutics 86:79-88 (1992).
A.K. Hilton & P.B. Deasy, "Use of Hyroxypropyl Methylcellulose Acetate Succinate in an Enteric Polymer Matrix to Design Controlled-Release Tablets of Amoxicillin Trihydrate," J. Pharm. Sciences 82(7):737-743 (1993).
J. Hirtz, "The Gastrointestinal Absorption of Drugs in Man: A Review of Current Concepts and Methods of Investigation," Br. J. Clin. Pharmac. 19:77S-83S (1985).
Ammon Hoffman et al., "Pharmacodynamic and Pharmacokinetic Rationales for the Development of an Oral Controlled-Release Amoxicillin Dosage Form," J. Controlled Release 54:29-37 (1998).
H. E. Huber et al., "Utilization of Hydrophilic Gums for the Control of Drug Release from Tablet Formulations I. Disintegration and Dissolution Behavior," J. Pharm. Sciences 55(9):974-976 (1966).

* cited by examiner

PHARMACEUTICAL FORMULATION

This application is a continuation of U.S. application Ser. No. 15/520,752, filed Apr. 20, 2017, which is a national phase entry of PCT/GB2015/053151, filed on Oct. 21, 2015, which claims the benefit of British Application No. 1506755.6, filed Apr. 21, 2015, and the benefit of U.S. Provisional Patent Application No. 62/066,532, filed on Oct. 21, 2014, the contents of each of which are incorporated by reference herein in their entirety.

FIELD OF THE INVENTION

The present invention relates to a novel pharmaceutical formulation.

In particular, the present invention is directed to a sustained release formulation for oral administration comprising guaifenesin, naproxen and at least one additional active drug ingredient.

RELATED ART

Pharmaceutical compositions comprising combinations of actives are well-known in the prior art. For example, many OTC cold & flu remedies include an anti-inflammatory together with an antitussive or cough suppressant. In addition, there are a number of pain killers which are based on a combination of one or more of ibuprofen, aspirin, paracetamol and codeine. There are also available immediate release products which combine more than two actives. For example, the TYLENOL® range includes products which combine paracetamol, dextromethorphan & guaifenesin. However, as these products are immediate release products re-dosing is required every 4 to 6 hours in order to maintain a therapeutic effect.

However, there is no specific teaching in the prior art of a sustained release dosage form containing guaifenesin, an analgesic and at least one other pharmaceutically active agent which is capable of sustaining a therapeutic effect for each of the actives for at least twelve hours.

Such a combination would be advantageous to develop as it would provide an individual relief from the symptoms of a cough, cold, or flu for an extended period of up to 12 hours. In particular, it would be desirable to develop a product which contains actives that can provide relief from the symptoms of a cough or cold as well as an analgesic. The low solubility of analgesics, however, can impact the dissolution of other active compounds in a combination product. This is particularly true in conventional extended release products where release control is dependent on the erosion of a polymer matrix.

In the area of solid single-dose combination products, such as tablets or caplets, most of the prior art is directed towards combinations of two different actives, each active being contained in a separate layer from the other with the third layer acting as a barrier to prevent any negative interactions between the active-containing layers.

WO 00/059479 discloses a novel pharmaceutical dosage form that provides pulsatile delivery of methylphenidate. WO 99/17745 describes a controlled-release monolithic system for oral administration comprising a disintegrating layer, an erodible layer and a swelling layer, of which two are external and one is intermediate, each layer containing one or more drugs.

DETAILED DESCRIPTION OF EMBODIMENTS OF THE INVENTION

According to a first aspect of the present invention there is provided a pharmaceutical composition comprising a pharmaceutically effective amount of at least three different pharmaceutical actives selected from expectorant, an analgesic and at least one further active which is selected to be an antitussive, a decongestant or an antihistamine wherein the composition provides a therapeutic effect in respect of each active for a period of up to 12 hours.

Typically the analgesic is selected to be an NSAID. The NSAID can be selected from naproxen, ketoprofen, diclofenac, ibuprofen or flurbiprofen.

The expectorant can be guaifenesin.

The at least one other drug can be selected from an antitussive such as dextromethorphan, codeine, codeine phosphate, codeine sulphate, diphenhydramine citrate, and diphenhydramine hydrochloride, a decongestant such as phenylephrine hydrochloride, phenylpropanolamine hydrochloride, pseudoephedrine or ephedrine, an antihistamine such as chlorpheniramine maleate, brompheniramine maleate, phenindamine tartrate, pyrilamine maleate, doxylamine succinate, phenyltoloxamine citrate, diphenhydramine hydrochloride, promethazine, and clemastine fumerate, or a combination thereof. Preferred actives are dextromethorphan or pseudoephedrine.

The total amount of expectorant can be from about 200 mg-2400 mg, preferably about 600 mg-1200 mg. A preferred amount of expectorant is 600 mg. In an alternative embodiment, a preferred amount is 1200 mg.

The total amount of analgesic can be from about 5-4000 mg, preferably 110-220 mg. A preferred amount of analgesic is 110 mg. In an alternative embodiment, a preferred amount is 220 mg.

When the other drug is selected to be dextromethorphan, the total amount of said dextromethorphan can be from about 10-120 mg, preferably 15-60 mg. More preferably, the amount of dextromethorphan is 25-35 mg. A preferred amount of dextromethorphan is 30 mg. In an alternative embodiment, a preferred amount is 60 mg.

When the at least one other drug is selected to be pseudoephedrine, the total amount of said pseudoephedrine can be from about 10-240 mg, preferably 60-120 mg.

In a preferred combination of pharmaceutically active ingredients the expectorant is guaifenesin, the analgesic is naproxen and the antitussive is dextromethorphan.

The ratio of guaifenesin:naproxen:dextromethorphan can be from about 40:8:1 to about 10:3:1. A preferred ratio from 22:4:1 to 17:3:1. A most preferred ratio is 20:3.67:1.

The ratio of guaifensin:naproxen can be from about 1:1 to about 10:1, preferably from about 2:1 to about 7:1, more preferably from about 4:1 to about 6:1. A preferred ratio is about 5.45:1.

The ratio of the naproxen:dextromethorphan can be from about 1:1 to about 10:1, preferably from about 2:1 to about 7:1, more preferably from about 3:1 to about 5:1. A preferred ratio is about 3.67:1.

When an active other than dextromethorphan is used the ratio of naproxen:antitussive/decongestant/antihistamine can be from 10:1 to 2:1.

When flurbiprofen is selected to be the analgesic, the ratio of expectorant:analgesic:antitussive/decongestant/antihistamine can be from 25:5:1 to 5:0.5:1. The ratio of expectorant:analgesic can be from 10:1 to 5:1. The ratio of analgesic:antitussive/decongestant/antihistamine can be from 1:1.5-1:0.2.

When ibuprofen is selected to be the analgesic, the ratio of expectorant:analgesic:antitussive/decongestant/antihistamine can be from 25:30:1 to 5:5:1. The ratio of expectorant:

analgesic can be from 1:1 to 1:5. The ratio of analgesic: antitussive/decongestant/antihistamine can be from 30:1-5: 1.

When diclofenac is selected to be the analgesic, the ratio of expectorant:analgesic:antitussive/decongestant/antihistamine can be from 25:5:1 to 5:0.5:1. The ratio of expectorant: analgesic can be from 20:1 to 5:1. The ratio of analgesic: antitussive/decongestant/antihistamine can be from 1:2-1: 0.2.

When ketoprofen is selected to be the analgesic, the ratio of expectorant:analgesic:antitussive/decongestant/antihistamine can be from 25:5:1 to 5:0.5:1. The ratio of expectorant: analgesic can be from 10:1 to 5:1. The ratio of analgesic: antitussive/decongestant/antihistamine can be from 1:1.5-1: 0.2.

The composition can be in the form of one or more tablets, caplets, or capsules, gel, elixir, suspension, syrup, emulsion, powder, or granules. Typically, the composition is in the form of either a soft capsule or a hard gel capsule. When the composition is in the form of more than one tablets or caplets, the more than one tablets or caplets are contained within a single capsule. The capsule can be made of any suitable material, but is typically made of a gelatin material, hydroxyl propyl methyl cellulose or an alginate. The capsule can be in the form of either a soft capsule or a hard gel capsule.

The composition can comprise immediate and sustained release portions. As set forth herein, "portion" means a part of a whole, either separated or integrated with it. Thus, a product with two or more portions may have, but does not necessarily require, separate or discrete structural elements. As further set forth herein "sustained release" refers to a type of "modified release", and these terms are used interchangeably throughout.

The analgesic can be incorporated into the composition such that it is the sole active in the portion in which it is contained.

Typically, the composition is provided with both sustained-release and immediate-release portions comprising the expectorant.

In a preferred embodiment the composition comprises a first immediate release portion which comprises guaifenesin and a decongestant or an antitussive, a second immediate release portion which comprises naproxen, and a sustained release portion which comprises guaifenesin and a decongestant or an antitussive. In further preferred embodiments the antitussive can be selected to be dextromethorphan or the decongestant can be selected to be pseudoephedrine.

According to a second aspect of the present invention there is provided a pharmaceutical composition comprising a pharmaceutically effective amount of guaifenesin, naproxen and at least one further active which is selected to be an antitussive, a decongestant or an antihistamine.

The at least one other drug can be selected from an antitussive such as dextromethorphan, codeine, codeine phosphate, codeine sulphate, diphenhydramine citrate, and diphenhydramine hydrochloride, a decongestant such as phenylephrine hydrochloride, phenylpropanolamine hydrochloride, pseudoephedrine or ephedrine, an antihistamine such as chlorpheniramine maleate, brompheniramine maleate, phenindamine tartrate, pyrilamine maleate, doxylamine succinate, phenyltoloxamine citrate, diphenhydramine hydrochloride, promethazine, and clemastine fumerate, or a combination thereof. Preferred actives are dextromethorphan or pseudoephedrine.

The total amount of guaifenesin can be from about 200 mg-2400 mg, preferably about 600 mg-1200 mg. A preferred amount of expectorant is 600 mg. In an alternative embodiment, a preferred amount is 1200 mg.

The total amount of naproxen can be from about 5-400 mg, preferably 110-220 mg. A preferred amount of analgesic is 110 mg. In an alternative embodiment, a preferred amount is 220 mg.

When the other drug is selected to be dextromethorphan, the total amount of said dextromethorphan can be from about 10-120 mg, preferably 15-60 mg. More preferably, the amount of dextromethorphan is 25-35 mg. A preferred amount of dextromethorphan is 30 mg. In an alternative embodiment, a preferred amount is 60 mg.

When the at least one other drug is selected to be pseudoephedrine, the total amount of said pseudoephedrine can be from about 10-240 mg, preferably 60-120 mg.

In a preferred combination of pharmaceutically active ingredients the expectorant is guaifenesin, the analgesic is naproxen and the antitussive is dextromethorphan.

The ratio of guaifenesin:naproxen:dextromethorphan can be from about 40:8:1 to about 10:3:1. A preferred ratio from 22:4:1 to 17:3:1. A most preferred ratio is 20:3.67:1.

The ratio of guaifensin:naproxen can be from about 1:1 to about 10:1, preferably from about 2:1 to about 7:1, more preferably from about 4:1 to about 6:1. A preferred ratio is about 5.45:1.

The ratio of the naproxen:dextromethorphan can be from about 1:1 to about 10:1, preferably from about 2:1 to about 7:1, more preferably from about 3:1 to about 5:1. A preferred ratio is about 3.67:1.

When an active other than dextromethorphan is used the ratio of naproxen:antitussive/decongestant/antihistamine can be from 10:1 to 2:1.

The composition can be in the form of one or more tablets, caplets, or capsules, gel, elixir, suspension, syrup, emulsion, powder, or granules. Typically, the composition is in the form of a capsule. When the composition is in the form of more than one tablets or caplets, the more than one tablets or caplets are contained within a single capsule. The capsule can be made of any suitable material, but is typically made of a gelatin material.

The composition can comprise immediate and sustained release portions.

Typically, the composition is provided with both sustained-release and immediate-release portions comprising the expectorant.

The naproxen can be incorporated into the composition such that it is the sole active in the portion in which it is contained.

Typically, the composition is provided with both sustained-release and immediate-release portions comprising guaifenesin.

In a preferred embodiment the composition comprises a first immediate release portion which comprises guaifenesin and a decongestant or an antitussive, a second immediate release portion which comprises naproxen, and a sustained release portion which comprises guaifenesin. In further preferred embodiments the antitussive can be selected to be dextromethorphan or the decongestant can be selected to be pseudoephedrine.

The composition can be in the form of a tablet, caplet, capsule, gel, elixir, suspension, syrup or emulsion. Typically, the composition is in the form of a capsule.

In a particularly preferred embodiment of the composition of the first and second embodiments, the composition comprises guaifenesin, naproxen and dextromethorphan.

The composition according to either of the first or second aspect can comprise:

(a) 50-85% Guaifenesin;
(b) up to 5% Dextromethorphan or a pharmaceutically acceptable salt thereof; and
(c) 5-30% Naproxen or a pharmaceutically acceptable salt thereof;

The composition according to either of the first or second aspect can comprise:
(a) 55-65% Guaifenesin;
(b) 1-5% Dextromethorphan or a pharmaceutically acceptable salt thereof;
(c) 5-15% Naproxen or a pharmaceutically acceptable salt thereof;
(d) 1-10% Controlled release polymers;
(e) 0.1-10% Binders;
(f) 0.1-5% Disintegrants;
(g) 5-25% Diluents; and
(h) up to 1% Lubricants.

A preferred embodiment of the composition according to either of the first or second aspect can comprise:
(a) 55-65% Guaifenesin;
(b) 1-5% Dextromethorphan or a pharmaceutically acceptable salt thereof;
(c) 5-15% Naproxen or a pharmaceutically acceptable salt thereof;
(d) 1-8% Hypromellose;
(e) 10-25% Microcrystalline cellulose;
(f) 0.1 to 2.5% Povidone;
(g) 0.1 to 4.0% Croscarmellose Sodium;
(h) 0.1 to 2.0% Hydroxy Ethyl Cellulose; and
(i) up to 1% Magnesium stearate.

An alternative preferred embodiment can comprise:
(a) 58-63% Guaifenesin;
(b) 2-3.5 Dextromethorphan or a pharmaceutically acceptable salt thereof;
(c) 10-12% Naproxen or a pharmaceutically acceptable salt thereof;
(d) 1-2% Hypromellose;
(e) 15-25% Microcrystalline cellulose;
(f) 1-2% Povidone;
(g) 0.5-2.5% Croscarmellose sodium;
(h) 0.5 to 1% Hydroxyethyl cellulose; and
(i) up to 0.5% Magnesium stearate.

In an alternative embodiment the composition can comprise:
(a) 55-65% Guaifenesin;
(b) 1-5% Dextromethorphan or a pharmaceutically acceptable salt thereof;
(c) 5-15% Naproxen or a pharmaceutically acceptable salt thereof;
(d) 1-8% Hypromellose;
(e) 10-25% Microcrystalline cellulose;
(f) 0.1 to 2.5% Povidone;
(g) 0.1 to 2.0% Carbomer;
(h) 0.1 2.0% Sodium Starch Glycolate;
(i) up to 1% Magnesium stearate; and An alternative preferred embodiment can comprise:
(a) 59-65% Guaifenesin;
(b) 3-5% Dextromethorphan or a pharmaceutically acceptable salt thereof;
(c) 10-12% Naproxen or a pharmaceutically acceptable salt thereof;
(d) 1-6% Hypromellose;
(e) 10-20% Microcrystalline cellulose;
(f) 0.3 to 1% Povidone;
(g) 0.5-1% Carbomer;
(h) 0.1 to 0.5% Sodium Starch Glycolate; and
(i) up to 1% Magnesium stearate.

An alternative preferred embodiment can comprise:
(a) 59-65 Guaifenesin;
(b) 3-5% Dextromethorphan or a pharmaceutically acceptable salt thereof;
(c) 10-12% Naproxen or a pharmaceutically acceptable salt thereof;
(d) 1-6% Hypromellose;
(e) 10-20% Microcrystalline cellulose;
(f) 0.3 to 1% Povidone;
(g) 0.5-1% Carbomer;
(h) 1-2% Croscarmellose sodium;
(i) 0.1 to 0.5% Sodium Starch Glycolate; and
(j) up to 1% Magnesium stearate.

An alternative preferred embodiment of the composition according to either of the first or second aspect can comprise:
(a) 64-69% Guaifenesin;
(b) 3-5% Dextromethorphan or a pharmaceutically acceptable salt thereof;
(c) 12-15% Naproxen or a pharmaceutically acceptable salt thereof;
(d) 3-5% Hypromellose;
(e) 9-15% Microcrystalline cellulose;
(f) 0.4-0.65% Povidone;
(g) 0.75-1.3% Carbomer;
(h) 0.5-1% Magnesium stearate; and
(i) 0.25-0.5% Sodium starch glycolate.

The composition can further comprise one or more of:
(j) 0.5-1.5% Lactose;
(k) 2.5-3.5% Sodium lauryl sulphate; and
(l) 0.1-1.5% Croscarmellose sodium.

An alternative preferred embodiment of the composition according to either of the first or second aspect can comprise:
(a) 64-69% Guaifenesin;
(b) 3-5% Dextromethorphan or a pharmaceutically acceptable salt thereof;
(c) 12-15% Naproxen or a pharmaceutically acceptable salt thereof;
(d) 0.1-0.6% Hypromellose;
(e) 9-15% Microcrystalline cellulose;
(f) 0.4-0.65% Povidone;
(g) 0.75-1.3% Carbomer;
(h) 0.5-1% Magnesium stearate; and
(i) 0.25-0.5% Sodium starch glycolate.

The composition can further comprise one or more of:
(j) 0.5-1.5% Lactose;
(k) 2.5-3.5% Sodium lauryl sulphate; and
(l) 0.1-1.5% Croscarmellose sodium.

An alternative preferred embodiment of the composition according to either of the first or second aspect can comprise:
(a) 63-66% Guaifenesin;
(b) 3-5% Dextromethorphan or a pharmaceutically acceptable salt thereof;
(c) 10-12% Naproxen or a pharmaceutically acceptable salt thereof;
(d) 1.75-3.0% Hypromellose;
(e) 11-13% Microcrystalline cellulose;
(f) 1-2% Povidone;
(g) 0.5-0.75% Croscarmellose Sodium;
(h) 1-2% Carbomer;
(i) 0.1-0.5% Magnesium stearate;
(j) 0.5-1.5% Lactose; and optionally
(k) 2-3% Sodium Lauryl Sulphate.

An alternative preferred embodiment of the composition according to either of the first or second aspect can comprise:
- (a) 64-66% Guaifenesin;
- (b) 3-5% Dextromethorphan or a pharmaceutically acceptable salt thereof;
- (c) 11-13% Naproxen or a pharmaceutically acceptable salt thereof;
- (d) 1.75-3.0% Hypromellose;
- (e) 6-8.5% Microcrystalline cellulose;
- (f) 1-2% Povidone;
- (g) 1-5% Croscarmellose Sodium;
- (h) 0.5-1% Carbomer;
- (i) 0.5-1% Magnesium stearate; and
- (j) 0.5-1% Crospovidone.

The composition can further include one or more of:
- (k) 2-3% Sodium Lauryl Sulphate; and
- (l) 6-7% Sodium Bicarbonate.

An alternative preferred embodiment of the composition according to either of the first or second aspect can comprise:
- (a) 64-66% Guaifenesin;
- (b) 3-5% Dextromethorphan or a pharmaceutically acceptable salt thereof;
- (c) 11-13% Naproxen or a pharmaceutically acceptable salt thereof;
- (d) 1.75-3.0% Hypromellose;
- (e) 6-8.5% Microcrystalline cellulose;
- (f) 1-2% Povidone;
- (g) 1-5% Croscarmellose Sodium;
- (h) 0.5-1% Carbomer; and
- (i) 0.5-1% Magnesium stearate.

An alternative preferred embodiment of the composition according to either of the first or second aspect can comprise:
- (a) 62-65% Guaifenesin;
- (b) 3-5% Dextromethorphan or a pharmaceutically acceptable salt thereof;
- (c) 11-13% Naproxen or a pharmaceutically acceptable salt thereof;
- (d) 1.75-3.0% Hypromellose;
- (e) 6-8.5% Microcrystalline cellulose;
- (f) 1-2% Povidone;
- (g) 1-5% Croscarmellose Sodium;
- (h) 0.5-1% Carbomer; and
- (i) 0.5-1% Magnesium stearate;
- (j) 2-3% Sodium Lauryl Sulphate; and
- (k) 5-8% Sodium Bicarbonate.

An alternative preferred embodiment of the composition according to either of the first or second aspect can comprise:
- (a) 58-60% Guaifenesin;
- (b) 2-3% Dextromethorphan or a pharmaceutically acceptable salt thereof;
- (c) 10-11% Naproxen or a pharmaceutically acceptable salt thereof;
- (d) 2-3% Hypromellose;
- (e) 7-8% Microcrystalline cellulose;
- (f) 1-2% Povidone;
- (g) 2-3% Croscarmellose Sodium;
- (h) 0.1-0.2% Magnesium stearate;
- (i) 0.5-1% Crospovidone;
- (j) 1-3% Hydroxyethyl cellulose;
- (k) 2-3% Sodium Lauryl Sulphate; and
- (l) 9-10% Sodium bicarbonate.

An alternative preferred embodiment of the composition according to either of the first or second aspect can comprise:
- (a) 64-66% Guaifenesin;
- (b) 3-5% Dextromethorphan or a pharmaceutically acceptable salt thereof;
- (c) 11-13% Naproxen or a pharmaceutically acceptable salt thereof;
- (d) 2-3% Hypromellose;
- (e) 6-7% Microcrystalline cellulose;
- (f) 1-2% Povidone;
- (g) 0.1-0.5% Magnesium stearate;
- (h) 7-10% Crospovidone; and
- (i) 1-3% Hydroxyethyl cellulose.

A preferred embodiment of the composition according to either of the first or second aspect consists essentially of:
- (a) 55-65% Guaifenesin;
- (b) 1-5% Dextromethorphan or a pharmaceutically acceptable salt thereof;
- (c) 5-15% Naproxen or a pharmaceutically acceptable salt thereof;
- (d) 1-8% Hypromellose;
- (e) 10-25% Microcrystalline cellulose;
- (f) 0.1 to 2.5% Povidone;
- (g) 0.1 to 4.0% Croscarmellose Sodium;
- (h) 0.1 to 2.0% Hydroxy Ethyl Cellulose; and
- (i) up to 1% Magnesium stearate.

An alternative preferred embodiment consists essentially of:
- (a) 58-63% Guaifenesin;
- (b) 2-3.5 Dextromethorphan or a pharmaceutically acceptable salt thereof;
- (c) 10-12% Naproxen or a pharmaceutically acceptable salt thereof;
- (d) 1-2% Hypromellose;
- (e) 15-25% Microcrystalline cellulose;
- (f) 1-2% Povidone;
- (g) 0.5-2.5% Croscarmellose sodium;
- (h) 0.5 to 1% Hydroxyethyl cellulose; and
- (i) up to 0.5% Magnesium stearate.

In an alternative embodiment the composition consists essentially of:
- (a) 55-65% Guaifenesin;
- (b) 1-5% Dextromethorphan or a pharmaceutically acceptable salt thereof;
- (c) 5-15% Naproxen or a pharmaceutically acceptable salt thereof;
- (d) 1-8% Hypromellose;
- (e) 10-25% Microcrystalline cellulose;
- (f) 0.1 to 2.5% Povidone;
- (g) 0.1 to 2.0% Carbomer;
- (h) 0.1 2.0% Sodium Starch Glycolate;
- (i) up to 1% Magnesium stearate; and An alternative preferred embodiment consists essentially of:
- (a) 59-65% Guaifenesin;
- (b) 3-5% Dextromethorphan or a pharmaceutically acceptable salt thereof;
- (c) 10-12% Naproxen or a pharmaceutically acceptable salt thereof;
- (d) 1-6% Hypromellose;
- (e) 10-20% Microcrystalline cellulose;
- (f) 0.3 to 1% Povidone;
- (g) 0.5-1% Carbomer;
- (h) 0.1 to 0.5% Sodium Starch Glycolate; and
- (i) up to 1% Magnesium stearate.

An alternative preferred embodiment consists essentially of:
- (a) 59-65 Guaifenesin;
- (b) 3-5% Dextromethorphan or a pharmaceutically acceptable salt thereof;
- (c) 10-12% Naproxen or a pharmaceutically acceptable salt thereof;
- (d) 1-6% Hypromellose;
- (e) 10-20% Microcrystalline cellulose;
- (f) 0.3 to 1% Povidone;
- (g) 0.5-1% Carbomer;
- (h) 1-2% Croscarmellose sodium;
- (i) 0.1 to 0.5% Sodium Starch Glycolate; and
- (j) up to 1% Magnesium stearate.

An alternative preferred embodiment of the composition according to either of the first or second aspect consists essentially of:
- (a) 64-69% Guaifenesin;
- (b) 3-5% Dextromethorphan or a pharmaceutically acceptable salt thereof;
- (c) 12-15% Naproxen or a pharmaceutically acceptable salt thereof;
- (d) 3-5% Hypromellose;
- (e) 9-15% Microcrystalline cellulose;
- (f) 0.4-0.65% Povidone;
- (g) 0.75-1.3% Carbomer;
- (h) 0.5-1% Magnesium stearate; and
- (i) 0.25-0.5% Sodium starch glycolate.

An alternative preferred embodiment of the composition according to either of the first or second aspect consists essentially of:
- (a) 64-69% Guaifenesin;
- (b) 3-5% Dextromethorphan or a pharmaceutically acceptable salt thereof;
- (c) 12-15% Naproxen or a pharmaceutically acceptable salt thereof;
- (d) 0.1-0.5% Hypromellose;
- (e) 9-15% Microcrystalline cellulose;
- (f) 0.4-0.65% Povidone;
- (g) 0.75-1.3% Carbomer;
- (h) 0.5-1% Magnesium stearate; and
- (i) 0.25-0.5% Sodium starch glycolate.

An alternative preferred embodiment of the composition according to either of the first or second aspect consists essentially of:
- (a) 64-69% Guaifenesin;
- (b) 3-5% Dextromethorphan or a pharmaceutically acceptable salt thereof;
- (c) 12-15% Naproxen or a pharmaceutically acceptable salt thereof;
- (d) 3-5% Hypromellose;
- (e) 9-15% Microcrystalline cellulose;
- (f) 0.4-0.65% Povidone;
- (g) 0.75-1.3% Carbomer;
- (h) 0.5-1% Magnesium stearate;
- (i) 0.25-0.5% Sodium starch glycolate;
- (j) 0.5-1.5% Lactose; and
- (k) 0.1-1.5% Croscarmellose sodium.

An alternative preferred embodiment of the composition according to either of the first or second aspect consists essentially of:
- (a) 64-69% Guaifenesin;
- (b) 3-5% Dextromethorphan or a pharmaceutically acceptable salt thereof;
- (c) 12-15% Naproxen or a pharmaceutically acceptable salt thereof;
- (d) 0.1-0.6% Hypromellose;
- (e) 9-15% Microcrystalline cellulose;
- (f) 0.4-0.65% Povidone;
- (g) 0.75-1.3% Carbomer;
- (h) 0.5-1% Magnesium stearate;
- (i) 0.25-0.5% Sodium starch glycolate;
- (j) 0.5-1.5% Lactose; and
- (k) 0.1-1.5% Croscarmellose sodium.

An alternative preferred embodiment of the composition according to either of the first or second aspect consists essentially of:
- (a) 63-66% Guaifenesin;
- (b) 3-5% Dextromethorphan or a pharmaceutically acceptable salt thereof;
- (c) 10-12% Naproxen or a pharmaceutically acceptable salt thereof;
- (d) 1.75-3.0% Hypromellose;
- (e) 11-13% Microcrystalline cellulose;
- (f) 1-2% Povidone;
- (g) 0.5-0.75% Croscarmellose Sodium;
- (h) 1-2% Carbomer;
- (i) 0.1-0.5% Magnesium stearate; and
- (j) 0.5-1.5% Lactose.

An alternative preferred embodiment of the composition according to either of the first or second aspect consists essentially of:
- (a) 64-69% Guaifenesin;
- (b) 3-5% Dextromethorphan or a pharmaceutically acceptable salt thereof;
- (c) 12-15% Naproxen or a pharmaceutically acceptable salt thereof;
- (d) 3-5% Hypromellose;
- (e) 9-15% Microcrystalline cellulose;
- (f) 0.4-0.65% Povidone;
- (g) 0.75-1.3% Carbomer;
- (h) 0.5-1% Magnesium stearate;
- (i) 0.25-0.5% Sodium starch glycolate;
- (j) 2-3.5% Sodium Lauryl Sulphate; and
- (k) 0.1-1.5% Croscarmellose sodium.

An alternative preferred embodiment of the composition according to either of the first or second aspect consists essentially of:
- (a) 64-69% Guaifenesin;
- (b) 3-5% Dextromethorphan or a pharmaceutically acceptable salt thereof;
- (c) 12-15% Naproxen or a pharmaceutically acceptable salt thereof;
- (d) 0.1-0.6% Hypromellose;
- (e) 9-15% Microcrystalline cellulose;
- (f) 0.4-0.65% Povidone;
- (g) 0.75-1.3% Carbomer;
- (h) 0.5-1% Magnesium stearate;
- (i) 0.25-0.5% Sodium starch glycolate;
- (j) 2-3.5% Sodium Lauryl Sulphate; and
- (k) 0.1-1.5% Croscarmellose sodium.

An alternative preferred embodiment of the composition according to either of the first or second aspect consists essentially of:
- (a) 64-69% Guaifenesin;
- (b) 3-5% Dextromethorphan or a pharmaceutically acceptable salt thereof;
- (c) 12-15% Naproxen or a pharmaceutically acceptable salt thereof;
- (d) 0.1-0.6% Hypromellose;
- (e) 9-15% Microcrystalline cellulose;
- (f) 0.4-0.65% Povidone;
- (g) 0.75-1.3% Carbomer;
- (h) 0.5-1% Magnesium stearate;

(i) 0.25-0.5% Sodium starch glycolate;
(j) 2-3.5% Sodium Lauryl Sulphate; and
(k) 0.1-1.5% Croscarmellose sodium.

An alternative preferred embodiment of the composition according to either of the first or second aspect consists essentially of:
(a) 63-66% Guaifenesin;
(b) 3-5% Dextromethorphan or a pharmaceutically acceptable salt thereof;
(c) 10-12% Naproxen or a pharmaceutically acceptable salt thereof;
(d) 1.75-3.0% Hypromellose;
(e) 11-13% Microcrystalline cellulose;
(f) 1-2% Povidone;
(g) 0.5-0.75% Croscarmellose Sodium;
(h) 1-2% Carbomer;
(i) 0.1-0.5% Magnesium stearate;
(j) 0.5-1.5% Lactose; and
(k) 2-3% Sodium Lauryl Sulphate.

An alternative preferred embodiment of the composition according to either of the first or second aspect consists essentially of:
(a) 64-66% Guaifenesin;
(b) 3-5% Dextromethorphan or a pharmaceutically acceptable salt thereof;
(c) 11-13% Naproxen or a pharmaceutically acceptable salt thereof;
(d) 1.75-3.0% Hypromellose;
(e) 6-8.5% Microcrystalline cellulose;
(f) 1-2% Povidone;
(g) 1-5% Croscarmellose Sodium;
(h) 0.5-1% Carbomer;
(i) 0.5-1% Magnesium stearate;
(j) 0.5-1% Crospovidone; and
(k) 2-3% Hypromellose.

An alternative preferred embodiment of the composition according to either of the first or second aspect consists essentially of:
(a) 64-66% Guaifenesin;
(b) 3-5% Dextromethorphan or a pharmaceutically acceptable salt thereof;
(c) 11-13% Naproxen or a pharmaceutically acceptable salt thereof;
(d) 1.75-3.0% Hypromellose;
(e) 6-8.5% Microcrystalline cellulose;
(f) 1-2% Povidone;
(g) 1-5% Croscarmellose Sodium;
(h) 0.5-1% Carbomer;
(i) 0.5-1% Magnesium stearate;
(j) 0.5-1% Crospovidone;
(k) 2-3% Hypromellose;
(l) 2-3% Sodium Lauryl Sulphate; and
(m) 6-7% Sodium Bicarbonate.

An alternative preferred embodiment of the composition according to either of the first or second aspect consists essentially of:
(a) 58-60% Guaifenesin;
(b) 2-3% Dextromethorphan or a pharmaceutically acceptable salt thereof;
(c) 10-11% Naproxen or a pharmaceutically acceptable salt thereof;
(d) 2-3% Hypromellose;
(e) 7-8% Microcrystalline cellulose;
(f) 1-2% Povidone;
(g) 2-3% Croscarmellose Sodium;
(h) 0.1-0.2% Magnesium stearate;
(i) 0.5-1% Crospovidone;
(j) 1-3% Hydroxyethyl cellulose;
(k) 2-3% Sodium Lauryl Sulphate; and
(l) 9-10% Sodium bicarbonate.

An alternative preferred embodiment of the composition according to either of the first or second aspect consists essentially of:
(a) 64-66% Guaifenesin;
(b) 3-5% Dextromethorphan or a pharmaceutically acceptable salt thereof;
(c) 11-13% Naproxen or a pharmaceutically acceptable salt thereof;
(d) 2-3% Hypromellose;
(e) 6-7% Microcrystalline cellulose;
(f) 1-2% Povidone;
(g) 0.1-0.5% Magnesium stearate;
(h) 7-10% Crospovidone; and
(i) 1-3% Hydroxyethyl cellulose.

An alternative preferred embodiment of the composition according to either of the first or second aspect consists essentially of:
(a) 62-65% Guaifenesin;
(b) 3-5% Dextromethorphan or a pharmaceutically acceptable salt thereof;
(c) 11-13% Naproxen or a pharmaceutically acceptable salt thereof;
(d) 1.75-3.0% Hypromellose;
(e) 6-8.5% Microcrystalline cellulose;
(f) 1-2% Povidone;
(g) 1-5% Croscarmellose Sodium;
(h) 0.5-1% Carbomer; and
(i) 0.5-1% Magnesium stearate;
(j) 2-3% Sodium Lauryl Sulphate; and
(k) 5-8% Sodium Bicarbonate.

An alternative preferred embodiment of the composition according to either of the first or second aspect consists essentially of:
(a) 64-66% Guaifenesin;
(b) 3-5% Dextromethorphan or a pharmaceutically acceptable salt thereof;
(c) 11-13% Naproxen or a pharmaceutically acceptable salt thereof;
(d) 1.75-3.0% Hypromellose;
(e) 6-8.5% Microcrystalline cellulose;
(f) 1-2% Povidone;
(g) 1-5% Croscarmellose Sodium;
(h) 0.5-1% Carbomer; and
(i) 0.5-1% Magnesium stearate.

According to a third aspect of the present invention there is provided a pharmaceutical dosage form which comprises at least 3 distinct portions wherein 2 of the portions have immediate release characteristics and a $3^{rd}$ has modified release characteristics wherein one of the immediate release portions comprises an expectorant and a second active which is an antitussive or a decongestant and the second immediate release portion comprises an analgesic having a half-life of twelve hours and wherein the modified release portion comprises guaifenesin and a second active which is an antitussive or a decongestant.

The dosage form can comprise a first composition which comprises both immediate and modified release portions of the expectorant and the second active which is an antitussive or a decongestant and a second composition which comprises an analgesic having a therapeutic effect of twelve hours.

The analgesic can be incorporated into the composition such that it is the sole active in the portion in which it is contained.

In preferred embodiments of the compositions of the first, second and third aspects of the present invention the analgesic-containing immediate release portion can comprise:
- (a) 50-52% Naproxen or a pharmaceutically acceptable salt thereof;
- (b) 35-40% Microcrystalline cellulose;
- (c) up to 5% Povidone;
- (d) 5-8% Croscarmellose sodium; and
- (e) up to 1% Magnesium stearate.

In alternative preferred embodiments of the compositions of the first, second and third aspects of the present invention the analgesic-containing immediate release portion can comprise:
- (a) 70-75% Naproxen or a pharmaceutically acceptable salt thereof;
- (b) 20-25% Microcrystalline cellulose;
- (c) up to 5% Povidone;
- (d) up to 1% Magnesium stearate.

In further alternative preferred embodiments of the compositions of the first, second and third aspects of the present invention the analgesic-containing immediate release portion can comprise:
- (a) 70-75% Naproxen or a pharmaceutically acceptable salt thereof;
- (b) 5-10% Microcrystalline cellulose;
- (c) up to 5% Povidone;
- (d) up to 1% Magnesium stearate;
- (e) 5-10% Lactose; and
- (f) up to 5% Croscarmellose sodium.

In further alternative preferred embodiments of the compositions of the first, second and third aspects of the present invention the analgesic-containing immediate release portion can comprise:
- (a) 70-75% Naproxen or a pharmaceutically acceptable salt thereof;
- (b) 5-10% Microcrystalline cellulose;
- (c) up to 5% Povidone;
- (d) up to 1% Magnesium stearate;
- (e) 5-10% Lactose; and
- (f) 5-10% Croscarmellose sodium.

In further alternative preferred embodiments of the compositions of the first, second and third aspects of the present invention the analgesic-containing immediate release portion can comprise:
- (a) 70-75% Naproxen or a pharmaceutically acceptable salt thereof;
- (b) 5-10% Microcrystalline cellulose;
- (c) up to 5% Povidone;
- (d) up to 1% Magnesium stearate;
- (e) up to 5% Lactose; and
- (f) 15-20% Sodium Lauryl Sulphate.

In further alternative preferred embodiments of the compositions of the first, second and third aspects of the present invention the analgesic-containing immediate release portion can comprise:
- (a) 70-75% Naproxen or a pharmaceutically acceptable salt thereof;
- (b) 5-10% Microcrystalline cellulose;
- (c) up to 5% Povidone;
- (d) up to 1% Magnesium stearate;
- (e) up to 2% Croscarmellose sodium; and
- (f) 15-20% Sodium Lauryl Sulphate.

In preferred embodiments of the compositions of the first, second and third aspects of the present invention the guaifenesin-containing immediate release portion can comprise:
- (a) 30-40% Guaifenesin;
- (b) up to 5% Dextromethorphan or a pharmaceutically acceptable salt thereof;
- (c) 50-60% Microcrystalline cellulose;
- (d) up to 7% Povidone;
- (e) up to 7% Croscarmellose sodium; and
- (f) up to 1% Magnesium stearate.

In alternative preferred embodiments of the compositions of the first, second and third aspects of the present invention preferred embodiments of the compositions of the present the guaifenesin-containing immediate release portion can comprise:
- (a) 40-50% Guaifenesin;
- (b) up to 5% Dextromethorphan or a pharmaceutically acceptable salt thereof;
- (c) 40-50% Microcrystalline cellulose;
- (d) up to 5% Hypromellose;
- (e) up to 5% Sodium starch glycolate; and
- (f) up to 1% Magnesium stearate.

In alternative preferred embodiments of the compositions of the first, second and third aspects of the present invention preferred embodiments of the compositions of the present the guaifenesin-containing immediate release portion can comprise:
- (a) 50-65% Guaifenesin;
- (b) up to 5% Dextromethorphan or a pharmaceutically acceptable salt thereof;
- (c) 25-40% Microcrystalline cellulose;
- (d) up to 5% Povidone;
- (e) up to 5% Croscarmellose sodium; and
- (f) up to 1% Magnesium stearate.

In preferred embodiments of the compositions of the first, second and third aspects of the present invention the modified release portion can comprise:
- (a) 80-90% Guaifenesin;
- (b) up to 5% Dextromethorphan or a pharmaceutically acceptable salt thereof;
- (c) up to 10% Hypromellose;
- (d) up to 5% Carbomer;
- (e) up to 1.55% Magnesium stearate.

In alternative preferred embodiments of the compositions of the first, second and third aspects of the present invention preferred embodiments of the compositions of the present invention the modified release portion can comprise:
- (a) 80-90% Guaifenesin;
- (b) 3-6% Dextromethorphan or a pharmaceutically acceptable salt thereof;
- (c) up to 5% Hypromellose;
- (d) up to 2% Hydroxy ethylcellulose;
- (e) up to 5% Microcrystalline cellulose;
- (f) up to 1% Magnesium stearate.

In alternative preferred embodiments of the compositions of the first, second and third aspects of the present invention preferred embodiments of the compositions of the present invention the modified release portion can comprise:
- (a) 80-90% Guaifenesin;
- (b) 3-6% Dextromethorphan or a pharmaceutically acceptable salt thereof;
- (c) up to 5% Hypromellose;
- (d) up to 5% Hydroxy ethylcellulose;
- (e) up to 5% Microcrystalline cellulose;
- (f) up to 1% Magnesium stearate.

In preferred embodiments of the compositions of the first, second and third aspects of the present invention the modified release portion can comprise:
- (a) 85-90% Guaifenesin;

(b) 4-5% Dextromethorphan or a pharmaceutically acceptable salt thereof;
(c) 3-6% Hypromellose;
(d) 1-3% Carbomer;
(e) 0.5-1% Magnesium stearate.

In preferred embodiments of the compositions of the first, second and third aspects of the present invention the modified release portion can comprise:
(a) 90-93% Guaifenesin;
(b) 4-6% Dextromethorphan or a pharmaceutically acceptable salt thereof;
(c) 1-3% Carbomer;
(d) 0.5-1% Magnesium stearate.

In preferred embodiments of the compositions of the first, second and third aspects of the present invention the analgesic-containing immediate release portion consists essentially of:
(a) 50-52% Naproxen or a pharmaceutically acceptable salt thereof;
(b) 35-40% Microcrystalline cellulose;
(c) up to 5% Povidone;
(d) 5-8% Croscarmellose sodium; and
(e) up to 1% Magnesium stearate.

In alternative preferred embodiments of the compositions of the first, second and third aspects of the present invention the analgesic-containing immediate release portion consists essentially of:
(a) 70-75% Naproxen or a pharmaceutically acceptable salt thereof;
(b) 20-25% Microcrystalline cellulose;
(c) up to 5% Povidone;
(d) up to 1% Magnesium stearate.

In further alternative preferred embodiments of the compositions of the first, second and third aspects of the present invention the analgesic-containing immediate release portion consists essentially of:
(a) 70-75% Naproxen or a pharmaceutically acceptable salt thereof;
(b) 5-10% Microcrystalline cellulose;
(c) up to 5% Povidone;
(d) up to 1% Magnesium stearate;
(e) 5-10% Lactose; and
(f) up to 5% Croscarmellose sodium.

In further alternative preferred embodiments of the compositions of the first, second and third aspects of the present invention the analgesic-containing immediate release portion consists essentially of:
(a) 70-75% Naproxen or a pharmaceutically acceptable salt thereof;
(b) 5-10% Microcrystalline cellulose;
(c) up to 5% Povidone;
(d) up to 1% Magnesium stearate;
(e) 5-10% Lactose; and
(f) 5-10% Croscarmellose sodium.

In further alternative preferred embodiments of the compositions of the first, second and third aspects of the present invention the analgesic-containing immediate release portion consists essentially of:
(a) 70-75% Naproxen or a pharmaceutically acceptable salt thereof;
(b) 5-10% Microcrystalline cellulose;
(c) up to 5% Povidone;
(d) up to 1% Magnesium stearate;
(e) up to 5% Lactose; and
(f) 15-20% Sodium Lauryl Sulphate.

In further alternative preferred embodiments of the compositions of the first, second and third aspects of the present invention the analgesic-containing immediate release portion consists essentially of:
(a) 70-75% Naproxen or a pharmaceutically acceptable salt thereof;
(b) 5-10% Microcrystalline cellulose;
(c) up to 5% Povidone;
(d) up to 1% Magnesium stearate;
(e) up to 2% Croscarmellose sodium; and
(f) 15-20% Sodium Lauryl Sulphate.

In preferred embodiments of the compositions of the first, second and third aspects of the present invention the guaifenesin-containing immediate release portion consists essentially of:
(a) 30-40% Guaifenesin;
(b) up to 5% Dextromethorphan or a pharmaceutically acceptable salt thereof;
(c) 50-60% Microcrystalline cellulose;
(d) up to 7% Povidone;
(e) up to 7% Croscarmellose sodium; and
(f) up to 1% Magnesium stearate.

In alternative preferred embodiments of the compositions of the first, second and third aspects of the present invention preferred embodiments of the compositions of the present the guaifenesin-containing immediate release portion consists essentially of:
(a) 40-50% Guaifenesin;
(b) up to 5% Dextromethorphan or a pharmaceutically acceptable salt thereof;
(c) 40-50% Microcrystalline cellulose;
(d) up to 5% Hypromellose;
(e) up to 5% Sodium starch glycolate; and
(f) up to 1% Magnesium stearate.

In alternative preferred embodiments of the compositions of the first, second and third aspects of the present invention preferred embodiments of the compositions of the present the guaifenesin-containing immediate release portion consists essentially of:
(a) 50-65% Guaifenesin;
(b) up to 5% Dextromethorphan or a pharmaceutically acceptable salt thereof;
(c) 25-40% Microcrystalline cellulose;
(d) up to 5% Povidone;
(e) up to 5% Croscarmellose sodium; and
(f) up to 1% Magnesium stearate.

In preferred embodiments of the compositions of the first, second and third aspects of the present invention the modified release portion consists essentially of:
(a) 80-90% Guaifenesin;
(b) up to 5% Dextromethorphan or a pharmaceutically acceptable salt thereof;
(c) up to 10% Hypromellose;
(d) up to 5% Carbomer;
(e) up to 1.55% Magnesium stearate.

In alternative preferred embodiments of the compositions of the first, second and third aspects of the present invention preferred embodiments of the compositions of the present invention the modified immediate release portion consists essentially of:
(a) 80-90% Guaifenesin;
(b) 3-6% Dextromethorphan or a pharmaceutically acceptable salt thereof;
(c) up to 5% Hypromellose;
(d) up to 2% Hydroxy ethylcellulose;
(e) up to 5% Microcrystalline cellulose;
(f) up to 1% Magnesium stearate.

In alternative preferred embodiments of the compositions of the first, second and third aspects of the present invention preferred embodiments of the compositions of the present invention the modified immediate release portion consists essentially of:
(a) 80-90% Guaifenesin;
(b) 3-6% Dextromethorphan or a pharmaceutically acceptable salt thereof;
(c) up to 5% Hypromellose;
(d) up to 5% Hydroxy ethylcellulose;
(e) up to 5% Microcrystalline cellulose;
(f) up to 1% Magnesium stearate.

In preferred embodiments of the compositions of the first, second and third aspects of the present invention the modified release portion consists essentially of:
(a) 85-90% Guaifenesin;
(b) 4-5% Dextromethorphan or a pharmaceutically acceptable salt thereof;
(c) 3-6% Hypromellose;
(d) 1-3% Carbomer;
(e) 0.5-1% Magnesium stearate.

In preferred embodiments of the compositions of the first, second and third aspects of the present invention the modified release portion consists essentially of:
(a) 90-93% Guaifenesin;
(b) 4-6% Dextromethorphan or a pharmaceutically acceptable salt thereof;
(c) 1-3% Carbomer;
(d) 0.5-1% Magnesium stearate.

For the avoidance of doubt the present disclosure covers all possible combinations of the preferred embodiments of the immediate release analgesic-containing portion, the immediate release guaifenesin-containing portion and the modified release containing portion to give a composition having each of an immediate release analgesic-containing portion, an immediate release guaifenesin-containing portion and a modified release containing portion.

Modified release polymers that can be used in the compositions of the present invention include Acacia, Adipic Acid, Agar, Alginic Acid, Aliphatic Polyesters, Calcium Alginate, Carbomer, Carrageenan, Castor Oil, Cellaburate, Cellulose Acetate, Ceratonia, Colophony, Copovidone, Glyceryl Behenate, Glyceryl Monooleate, Glyceryl Monostearate, Glyceryl Palmitostearate, Hydroxypropyl Betadex, Hydroxypropyl Cellulose, Hydroxyethyl Cellulose, Hypromellose, Hypromellose Acetate Succinate, Methylcellulose, Polacrilin Potassium, Polycarbophil, Polydextrose, Polymethacrylates, Polyoxylglycerides, Polyvinyl Acetate Dispersion, Shellac, Sodium Alginate, Sodium Hyaluronate, Modified Starch, Sucrose Stearate, Microcrystalline Wax, White Wax, Yellow Wax, Xanthan Gum, Zein.

Hydrophilic polymers suitable for use in the sustained release portion include: one or more natural or partially or totally synthetic hydrophilic gums such as acacia, gum tragacanth, locust bean gum, guar gum, or karaya gum, modified cellulosic substances such as methylcellulose, hydroxymethylcellulose, hydroxypropyl methylcellulose, hydroxyethyl cellulose, hydroxypropyl cellulose, hydroxyethylcellulose, carboxyethylcellulose; proteinaceous substances such as agar, pectin, carrageen, and alginates; and other hydrophilic polymers such as carboxypolymethylene, gelatin, casein, zein, bentonite, magnesium aluminium silicate, polysaccharides, modified starch derivatives, and other hydrophilic polymers known to those of skill in the art or a combination of such polymers.

These hydrophilic polymers gel and dissolve slowly in aqueous acidic media thereby allowing the guaifenesin to diffuse from the gel in the stomach. When the gel reaches the intestines, it dissolves in controlled quantities in the higher pH medium, where the guaifenesin itself is fairly absorbable, to allow sustained release of guaifenesin throughout the digestive tract. Preferred hydrophilic polymers are the hydroxypropyl methylcelluloses such as those manufactured by The Dow Chemical Company and known as METHOCEL ethers. In one preferred embodiment of a sustained release formulation the hydrophilic polymer is a METHOCEL ether known as METHOCEL E10M.

Water-insoluble polymers which are suitable for use in the sustained release portion are polymers which generally do not dissolve in solutions of a pH below 5, and dissolve more slowly in basic solutions than the hydrophilic polymer. Because the polymer is insoluble in low pH environments such as those found in gastric fluid, it aids in retarding drug release in those regions. Likewise, because the polymer dissolves more slowly in solutions of higher pH than hydrophilic polymers, it aids in retarding drug release throughout the intestines. This overall delayed release results in a more uniform serum concentration of guaifenesin.

The water-insoluble polymers suitable for use in the sustained release portion include: polyacrylic acids, acrylic resins, acrylic latex dispersions, cellulose acetate phthalate, polyvinyl acetate phthalate, hydroxypropyl methylcellulose phthalate, carbomer and other polymers common to those of skill in the art. In a preferred embodiment, a sustained release formulation comprises the acrylic resin CARBOPOL 974P supplied by BF Goodrich.

The sustained release portion of the present invention may further comprise pharmaceutical additives including, but not limited to: lubricants such as magnesium stearate, calcium stearate, zinc stearate, powdered stearic acid, hydrogenated vegetable oils, talc, polyethylene glycol, and mineral oil; colorants such as Emerald Green Lake and various FD&C colors; binders such as sucrose, lactose, gelatin, starch paste, acacia, tragacanth, povidone polyethylene glycol, Pullulan and corn syrup; glidants such as colloidal silicon dioxide and talc; surface active agents such as sodium lauryl sulfate, dioctyl sodium sulfosuccinate, triethanolamine, polyoxyethylene sorbitan, poloxalkol, and quarternary ammonium salts; preservatives and stabilizers; excipients such as lactose, mannitol, glucose, fructose, xylose, galactose, sucrose, maltose, xylitol, sorbitol, chloride, sulfate and phosphate salts of potassium, sodium, and magnesium; and/or any other pharmaceutical additives known to those of skill in the art.

Colorants include, but are not limited to, Emerald Green Lake, FD&C Red #40, FD&C Yellow #6, FD&C Yellow #10, or FD&C Blue #1. In one preferred embodiment, a sustained release portion further comprises magnesium stearate and Emerald Green Lake. In another preferred embodiment, a sustained release formulation further comprises magnesium stearate and FD&C Blue #1 Aluminium Lake Dye.

The immediate release portion may comprise guaifenesin and various pharmaceutical additives such as disintegrants, lubricants, colorants, binders, glidants, surface active agents, preservatives, stabilizers, as described above and/or any other pharmaceutical additives known to those of skill in the art. Examples of suitable lubricant are as follows: Calcium Stearate, Glyceryl Behenate, Leucine, Magnesium Stearate, Mineral Oil, Myristic Acid, Palm Oil, Palmitic Acid, Poloxamer, Polyethylene Glycol, Potassium Benzoate, Sodium Benzoate, Sodium Lauryl Sulfate, Sodium Stearate, Sodium Stearyl Fumarate, Stearic Acid, Sucrose Stearate, Talc, Vegetable Oil, Zinc Stearate. Examples of suitable disintegrants are as follows: Carboxymethylcellulose Calcium, Carboxymethylcellulose Sodium, Sodium Lauryl Sulphate, Sodium Bicarboant, Chitosan, Coilloidal Sillicon Dioxide, Croscarmellose Sodium, Crospovidone, Glycine, Guar Gum, Lactose, Magnesium Aluminum Silicate, Polacrilin Potassium, Povidone, Sodium Alginate, Sodium Starch Glycolate. Examples of suitable diluents are as follows: Calcium Carbonate, Calcium Lactate, Calcium Phosphate, Calcium Silicate, Calcium Sulfate, Cellaburate, Cellulose Acetate, Microcrystalline Cellulose, Silicified Microcrystalline Cellulose, Corn Syrup Solids, Dextrates, Dextrin, Dextrose, Erythritol, Ethylcellulose, Fructose, Inulin, Isomalt, Kaolin, Lactitol, Lactose, Magnesium Carbonate, Magnesium Oxide, Maltitol, Maltodextrin, Maltose, Mannitol, Triglycerides, Polydextrose, Simethicone, Sodium Bicarbonate, Sodium Carbonate, Sodium Chloride, Sorbitol, Sucrose, Sugar, Sulfobutylether β-Cyclodextrin, Sunflower Oil, Talc, Trehalose, Xylitol. Examples of suitable binders are as follows: Attapulgite, Calcium Carbonate, Calcium Lactate, Ceratonia, Colophony, Copovidone, Ethylcellulose, Ethylene Glycol and Vinyl Alcohol Grafted Copolymer, Gelatin, Glucose, Hydroxethylmethyl Celluose, Magnesium Aluminium Silicate, Methylcellulose, Polycarbophil, Polydextrose, Polyethylene Oxide, Polymethacrylates, Povidone, Pullulan, Vitamin E Polyethylene Glycol Succinate.

For the avoidance of any doubt, reference to a pharmaceutically active compound includes all enantiomers and stereoisomers thereof, and also all pharmaceutically acceptable salts or esters thereof. For example, naproxen includes naproxen sodium, pseudoephedrine includes pseudoephedrine hydrochloride, dextromethorphan includes dextromethorphan hydrobromide.

In an alternative embodiment, the immediate release portion which comprises guaifenesin may further comprise the additional or more actives in the form of a drug/active-resin complex.

According to a fourth aspect of the present invention there is provided a sustained-release polymer matrix which consists essentially of a combination of a hydroxy propyl methyl cellulose having a molecular weight of 100,000-500,000 and a hydroxyethyl cellulose having a molecular weight of 500,000-2,000,000.

The molecular weight of hydroxyl propyl methyl cellulose can 200,000 to 300,000. A preferred molecular weight is 250,000.

The molecular weight of hydroxyethyl cellulose can 1,000,000 to 1,500,000. A preferred molecular weight is 1,300,000.

The ratio of the hydroxyl propyl methyl cellulose:hydroxyethyl cellulose is from 1:1 to 3:1. A preferred ratio is from 2:1 to 2.5:1. A more preferred ratio is 2.1:1.

According to a fifth aspect of the present invention there is provided the use of a sustained release polymer matrix as described in the fourth aspect in a pharmaceutical formulation.

The pharmaceutical formulation can comprise at least one active selected from an expectorant, an analgesic, an antihistamine, an antitussive, or a decongestant. The expectorant can be selected to be guaifenesin or n-acetyl cysteine. The analgesic can be selected to be naproxen, ketoprofen, diclofenac, ibuprofen and flurbiprofen. The antitussive can be selected to be dextromethorphan, codeine, codeine phosphate, codeine sulphate, diphenhydramine citrate, and diphenhydramine hydrochloride. The decongestant can be selected to be phenylephrine hydrochloride, phenylpropanolamine hydrochloride, pseudoephedrine or ephedrine. The antihistamine can be selected to be chlorpheniramine maleate, brompheniramine maleate, phenindamine tartrate, pyrilamine maleate, doxylamine succinate, phenyltoloxamine citrate, diphenhydramine hydrochloride, promethazine, and clemastine fumerate, or a combination thereof.

According to a sixth aspect of the present invention there is provided a method of providing relief from the symptoms of bronchial conditions, coughing and symptoms or diseases associated with coughing comprising administering to an individual a composition as described in the first, second or third aspects of the present invention.

According to a seventh aspect of the present invention there is provided the use of a composition as described in the first, second or third aspects of the present invention for the preparation of a medicament for the treatment of bronchial conditions, coughing and diseases associated with coughing.

According to an eighth aspect of the present invention these is provided an immediate release formulation of naproxen having an improved dissolution profile.

In a preferred embodiment the composition can comprise:
(a) 50-52% Naproxen or a pharmaceutically acceptable salt thereof;
(b) 35-40% Microcrystalline cellulose;
(c) up to 5% Povidone;
(d) 5-8% Croscarmellose sodium; and
(e) up to 1% Magnesium stearate.

In a further preferred embodiment the composition can comprise:
(a) 70-75% Naproxen or a pharmaceutically acceptable salt thereof;
(b) 20-25% Microcrystalline cellulose;
(c) up to 5% Povidone;
(d) up to 1% Magnesium stearate.

In a further preferred embodiment the composition can comprise:
(a) 70-75% Naproxen or a pharmaceutically acceptable salt thereof;
(b) 5-10% Microcrystalline cellulose;
(c) up to 5% Povidone;
(d) up to 1% Magnesium stearate;
(e) 5-10% Lactose; and
(f) up to 5% Croscarmellose sodium.

In a further preferred embodiment the composition can comprise:
(a) 70-75% Naproxen or a pharmaceutically acceptable salt thereof;
(b) 5-10% Microcrystalline cellulose;
(c) up to 5% Povidone;
(d) up to 1% Magnesium stearate;
(e) 5-10% Lactose; and
(f) 5-10% Croscarmellose sodium.

In a further preferred embodiment the composition can comprise:
(a) 70-75% Naproxen or a pharmaceutically acceptable salt thereof;
(b) 5-10% Microcrystalline cellulose;
(c) up to 5% Povidone;
(d) up to 1% Magnesium stearate;
(e) up to 5% Lactose; and
(f) 15-20% Sodium Lauryl Sulphate.

In a further preferred embodiment the composition can comprise:
(a) 70-75% Naproxen or a pharmaceutically acceptable salt thereof;
(b) 5-10% Microcrystalline cellulose;
(c) up to 5% Povidone;
(d) up to 1% Magnesium stearate;
(e) up to 2% Croscarmellose sodium; and (f) 15-20% Sodium Lauryl Sulphate.

In a further preferred embodiment the composition can consist essentially of:
  (a) 50-52% Naproxen or a pharmaceutically acceptable salt thereof;
  (b) 35-40% Microcrystalline cellulose;
  (c) up to 5% Povidone;
  (d) 5-8% Croscarmellose sodium; and
  (e) up to 1% Magnesium stearate.

In a further preferred embodiment the composition can consist essentially of:
  (a) 70-75% Naproxen or a pharmaceutically acceptable salt thereof;
  (b) 20-25% Microcrystalline cellulose;
  (c) up to 5% Povidone;
  (d) up to 1% Magnesium stearate.

In a further preferred embodiment the composition can consist essentially of:
  (a) 70-75% Naproxen or a pharmaceutically acceptable salt thereof;
  (b) 5-10% Microcrystalline cellulose;
  (c) up to 5% Povidone;
  (d) up to 1% Magnesium stearate;
  (e) 5-10% Lactose; and
  (f) up to 5% Croscarmellose sodium.

In a further preferred embodiment the composition can consist essentially of:
  (a) 70-75% Naproxen or a pharmaceutically acceptable salt thereof;
  (b) 5-10% Microcrystalline cellulose;
  (c) up to 5% Povidone;
  (d) up to 1% Magnesium stearate;
  (e) 5-10% Lactose; and
  (f) 5-10% Croscarmellose sodium.

In a further preferred embodiment the composition can consist essentially of:
  (a) 70-75% Naproxen or a pharmaceutically acceptable salt thereof;
  (b) 5-10% Microcrystalline cellulose;
  (c) up to 5% Povidone;
  (d) up to 1% Magnesium stearate;
  (e) up to 5% Lactose; and
  (f) 15-20% Sodium Lauryl Sulphate.

In a further preferred embodiment the composition can consist essentially of:
  (a) 70-75% Naproxen or a pharmaceutically acceptable salt thereof;
  (b) 5-10% Microcrystalline cellulose;
  (c) up to 5% Povidone;
  (d) up to 1% Magnesium stearate;
  (e) up to 2% Croscarmellose sodium; and
  (f) 15-20% Sodium Lauryl Sulphate.

Typically, the composition has a dissolution profile of 68-70% after 10 mins and 93-98% after 20 mins when tested using US Pharmacopoeia apparatus 2 (paddles at 75 rpm at 37° C.) in Fessif media at pH 5.

Typically, the composition has a dissolution profile of 85-90% after 10 mins when tested using US Pharmacopoeia apparatus 2 (paddles at 75 rpm at 37° C.) in Fessif media at pH 6.8.

Fessif is a term used in the art to mean Fed State Simulated Intestinal Fluid. Fassif is a term used in the art to mean Fasted State Simulated Intestinal Fluid.

As used herein, the term "about" means that the numerical value is approximate and small variations would not significantly affect the practice of the disclosed embodiments. Where a numerical limitation is used, unless indicated otherwise by the context, "about" means the numerical value can vary by +10% and remain within the scope of the disclosed embodiments.

As used herein, the term "consisting essentially of" means the composition contains the indicated components and may contain additional components provided that the additional components that are non-active and do not materially affect the composition's basic characteristics. As used herein, the term "consisting of" means the composition contains the only indicated components and excludes other components.

As used herein, the term "up to" means a value greater than zero. For example, the term "up to 1%" means that component is present in the composition and can be present to an amount of 1%. The term "up to 5%" means that the component is present in the composition and can be present to an amount of 5%.

For the avoidance of doubt when the composition of the present invention is in the form of a tablet or tablets, the values given for both the ranges and amounts of the components in the compositions of the present invention refer to uncoated tablets. Additional coatings can be added as required.

Embodiments of the present invention will now be described by way of example only.

Example 1

| Tablet 1: Naproxen | | |
| --- | --- | --- |
| Ingredient | mg/tablet | % Weight |
| Naproxen Sodium | 110.0 mg | 73.33% |
| Microcrystalline Cellulose | 34.45 mg | 22.96% |
| Povidone | 4.50 mg | 3.0% |
| Mg Stearate | 1.05 mg | 0.7% |
| Total Tablet | 150.0 mg | 100.0% |

| Tablet 2: Immediate/Sustained Release Dextromethorphan and Guaifenesin | | |
| --- | --- | --- |
| Ingredient | mg/tablet | % Weight |
| Guaifenesin | 600.0 mg | 76.41% |
| Hypromellose | 50.00 mg | 6.37% |
| MCC | 87.52 mg | 11.15% |
| Dextromethorphan HBr | 30.0 mg | 3.82% |
| Carbomer | 7.50 mg | 0.96% |
| Sodium Starch Glycolate | 3.98 mg | 0.51% |
| Colourant | 0.20 mg | 0.025% |
| Mg Stearate | 6.0 mg | 0.76% |
| Total Tablet | 785.2 mg | 100.0% |

Example 2

| Tablet 1: Naproxen | | |
| --- | --- | --- |
| Ingredient | mg/tablet | % Weight |
| Naproxen Sodium | 110.0 mg | 51.16% |
| Microcrystalline Cellulose | 81.00 mg | 37.67% |
| Crospovidone | 7.50 mg | 3.49% |
| Croscarmellose sodium | 15.00 mg | 6.98% |
| Mg Stearate | 1.50 mg | 0.7% |
| Total Tablet | 215.0 mg | 100.0% |

Tablet 2: Immediate/Sustained Release Dextromethorphan and Guaifenesin

| Ingredient | mg/tablet | % Weight |
|---|---|---|
| Guaifenesin | 600.0 mg | 74.77% |
| Hypromellose | 19.00 mg | 2.37% |
| MCC | 129.40 mg | 16.12% |
| Dextromethorphan HBr | 30.0 mg | 3.74% |
| Povidone | 7.00 mg | 0.87% |
| Croscarmellose Sodium | 6.00 mg | 0.74% |
| Hydroxy ethyl cellulose | 9.00 mg | 1.12% |
| Colourant | 0.20 mg | 0.025% |
| Mg Stearate | 1.9 mg | 0.24% |
| Total Layer | 802.5 mg | 100.0% |

Example 3

Tablet 1: Naproxen

| Ingredient | mg/tablet | % Weight |
|---|---|---|
| Naproxen Sodium | 110.0 mg | 73.33% |
| Microcrystalline Cellulose | 14.55 mg | 9.7% |
| Lactose | 12.65 mg | 8.4% |
| Povidone | 4.65 mg | 3.1% |
| Croscarmellose sodium | 7.15 mg | 4.8% |
| Mg Stearate | 1 mg | 0.7% |
| Total Tablet | 150.0 mg | 100.0% |

Tablet 2: Immediate/Modified Release Dextromethorphan and Guaifenesin

| Ingredient | mg/tablet | % Weight |
|---|---|---|
| Immediate Release Layer | | |
| Guaifenesin | 200 mg | 63.77% |
| Dextromethorphan HBr | 10 mg | 3.19% |
| Microcrystalline Cellulose | 85 mg | 27.10% |
| Povidone | 10 mg | 3.19% |
| Croscarmellose Sodium | 8.5 mg | 2.71% |
| Mg Stearate | 0.15 mg | 0.05% |
| Total Layer | 313.65 mg | 100.00% |
| Modified Release Layer | | |
| Guaifenesin | 400 mg | 84.54% |
| Dextromethorphan HBr | 20 mg | 4.23% |
| Hypromellose (K100M) | 24.5 mg | 5.18% |
| Hydroxyethylcellulose | 12.25 mg | 2.59% |
| Microcrystalline Cellulose | 14.75 mg | 3.12% |
| Colourant | 0.1 mg | 0.02% |
| Mg Stearate | 1.55 mg | 0.33% |
| Total Layer | 473.15 mg | 100.00% |
| Total Tablet | 786.8 mg | 100.0% |

Example 4

Tablet 1: Naproxen

| Ingredient | mg/tablet | % Weight |
|---|---|---|
| Naproxen Sodium | 110 mg | 73.33% |
| Microcrystalline Cellulose | 6 mg | 4.00% |
| Lactose | 5 mg | 3.33% |
| Povidone | 3 mg | 2.00% |
| Sodium lauryl sulfate | 25 mg | 16.67% |
| Mg Stearate | 1 mg | 0.67% |
| Total Tablet | 150.0 mg | 100.0% |

Tablet 2: Immediate/Modified Release Dextromethorphan and Guaifenesin

| Ingredient | mg/tablet | % Weight |
|---|---|---|
| Immediate Release Layer | | |
| Guaifenesin | 200 mg | 63.77% |
| Dextromethorphan HBr | 10 mg | 3.19% |
| Microcrystalline Cellulose | 85 mg | 27.10% |
| Povidone | 10 mg | 3.19% |
| Croscarmellose Sodium | 8.5 mg | 2.71% |
| Mg Stearate | 0.15 mg | 0.05% |
| Total Layer | 313.65 mg | 100.00% |
| Modified Release Layer | | |
| Guaifenesin | 400 mg | 84.54% |
| Dextromethorphan HBr | 20 mg | 4.23% |
| Hypromellose (K100M) | 24.5 mg | 5.18% |
| Hydroxyethylcellulose | 12.25 mg | 2.59% |
| Microcrystalline Cellulose | 14.75 mg | 3.12% |
| Colourant | 0.1 mg | 0.02% |
| Mg Stearate | 1.55 mg | 0.33% |
| Total Layer | 473.15 mg | 100.00% |
| Total Tablet | 786.8 mg | 100.0% |

Example 5

Tablet 1: Naproxen

| Ingredient | mg/tablet | % Weight |
|---|---|---|
| Naproxen Sodium | 110.0 mg | 73.33% |
| Microcrystalline Cellulose | 14.55 mg | 9.7% |
| Lactose | 12.65 mg | 8.4% |
| Povidone | 4.65 mg | 3.1% |
| Croscarmellose sodium | 7.15 mg | 4.8% |
| Mg Stearate | 1 mg | 0.7% |
| Total Tablet | 150.0 mg | 100.0% |

Tablet 2: Immediate/Modified Release Dextromethorphan and Guaifenesin

| Ingredient | mg/tablet | % Weight |
|---|---|---|
| Immediate Release Layer | | |
| Guaifenesin | 130 mg | 54.83% |
| Dextromethorphan HBr | 7.00 mg | 2.95% |
| Microcrystalline Cellulose | 85.00 mg | 35.85% |
| Povidone | 8.00 mg | 3.37% |

-continued

Tablet 2: Immediate/Modified Release Dextromethorphan and Guaifenesin

| Ingredient | mg/tablet | % Weight |
|---|---|---|
| Croscarmellose Sodium | 7.00 mg | 2.95% |
| Mg Stearate | 0.10 mg | 0.04% |
| Total Layer | 237.10 mg | 100.00% |
| Modified Release Layer | | |
| Guaifenesin | 470 mg | 86.35% |
| Dextromethorphan HBr | 23 mg | 4.23% |
| Hypromellose (K100M) | 17 mg | 3.12% |
| Hydroxyethylcellulose | 17 mg | 3.12% |
| Microcrystalline Cellulose | 15.5 mg | 2.85% |
| Colourant | 0.1 mg | 0.02% |
| Mg Stearate | 1.7 mg | 0.31% |
| Total Layer | 544.3 mg | 100.00% |
| Total Tablet | 781.40 mg | 100.0% |

Example 6

Tablet 1: Naproxen

| Ingredient | mg/tablet | % Weight |
|---|---|---|
| Naproxen Sodium | 110 mg | 73.33% |
| Microcrystalline Cellulose | 6 mg | 4.00% |
| Lactose | 5 mg | 3.33% |
| Povidone | 3 mg | 2.00% |
| Sodium lauryl sulfate | 25 mg | 16.67% |
| Mg Stearate | 1 mg | 0.67% |
| Total Tablet | 150.0 mg | 100.0% |

Tablet 2: Immediate/Modified Release Dextromethorphan and Guaifenesin

| Ingredient | mg/tablet | % Weight |
|---|---|---|
| Immediate Release Layer | | |
| Guaifenesin | 130 mg | 54.83% |
| Dextromethorphan HBr | 7.00 mg | 2.95% |
| Microcrystalline Cellulose | 85.00 mg | 35.85% |
| Povidone | 8.00 mg | 3.37% |
| Croscarmellose Sodium | 7.00 mg | 2.95% |
| Mg Stearate | 0.10 mg | 0.04% |
| Total Layer | 237.10 mg | 100.00% |
| Modified Release Layer | | |
| Guaifenesin | 470 mg | 86.35% |
| Dextromethorphan HBr | 23 mg | 4.23% |
| Hypromellose (K100M) | 17 mg | 3.12% |
| Hydroxyethylcellulose | 17 mg | 3.12% |
| Microcrystalline Cellulose | 15.5 mg | 2.85% |
| Colourant | 0.1 mg | 0.02% |
| Mg Stearate | 1.7 mg | 0.31% |
| Total Layer | 544.3 mg | 100.00% |
| Total Tablet | 781.40 mg | 100.0% |

Example 7

Tablet 1: Naproxen

| Ingredient | mg/tablet | % Weight |
|---|---|---|
| Naproxen Sodium | 110 mg | 73.33% |
| Microcrystalline Cellulose | 34.45 mg | 22.97% |
| Povidone | 4.5 mg | 3.00% |
| Mg Stearate | 1.05 mg | 0.7% |
| Total Tablet | 150.0 mg | 100.0% |

Tablet 2: Immediate/Modified Release Dextromethorphan and Guaifenesin

| Ingredient | mg/tablet | % Weight |
|---|---|---|
| Immediate Release Layer | | |
| Guaifenesin | 85.5 mg | 47.50% |
| Dextromethorphan HBr | 6.75 mg | 3.75% |
| Microcrystalline Cellulose | 78.77 mg | 43.76% |
| Hypromellose | 4.50 mg | 2.50% |
| Sodium Starch Glycolate | 3.58 mg | 1.99% |
| Mg Stearate | 0.90 mg | 0.50% |
| Total Layer | 180.00 mg | 100.00% |
| Modified Release Layer | | |
| Guaifenesin | 514.50 mg | 88.83% |
| Dextromethorphan HBr | 23.25 mg | 4.03% |
| Hypromellose | 27.50 mg | 4.75% |
| Carbomer | 8.25 mg | 1.42% |
| Colourant | 0.22 mg | 0.04 % |
| Mg Stearate | 5.50 mg | 0.95% |
| Total Layer | 579.22 mg | 100.00% |
| Total Tablet | 759.22 mg | 100.0% |

Example 8

Tablet 1: Naproxen

| Ingredient | mg/tablet | % Weight |
|---|---|---|
| Naproxen Sodium | 110 mg | 73.33% |
| Microcrystalline Cellulose | 34.45 mg | 22.97% |
| Povidone | 4.5 mg | 3.00% |
| Mg Stearate | 1.05 mg | 0.7% |
| Total Tablet | 150.0 mg | 100.0% |

Tablet 2: Immediate/Modified Release Dextromethorphan and Guaifenesin

| Ingredient | mg/tablet | % Weight |
|---|---|---|
| Immediate Release Layer | | |
| Guaifenesin | 76.00 mg | 47.50% |
| Dextromethorphan HBr | 6.00 mg | 3.75% |
| Microcrystalline Cellulose | 70.02 mg | 43.76% |
| Hypromellose | 4.00 mg | 2.50% |

-continued

Tablet 2: Immediate/Modified Release
Dextromethorphan and Guaifenesin

| Ingredient | mg/tablet | % Weight |
|---|---|---|
| Sodium Starch Glycolate | 3.18 mg | 1.99% |
| Mg Stearate | 0.80 mg | 0.50% |
| Total Layer | 160.00 mg | 100.00% |
| Modified Release Layer | | |
| Guaifenesin | 424.00 mg | 91.74% |
| Dextromethorphan HBr | 24.00 mg | 5.19% |
| Carbomer | 9.90 mg | 2.14% |
| Colourant | 0.26 mg | 0.06% |
| Mg Stearate | 4.00 mg | 0.87% |
| Total Layer | 462.16 mg | 100.00% |
| Total Tablet | 622.16 mg | 100.0% |

Example 9

Tablet 1: Naproxen

| Ingredient | mg/tablet | % Weight |
|---|---|---|
| Naproxen Sodium | 110 mg | 73.33% |
| Microcrystalline Cellulose | 14.5 mg | 9.67% |
| Povidone | 4.75 mg | 3.17% |
| Mg Stearate | 0.75 mg | 0.7% |
| Lactose | 10.00 mg | 6.67% |
| Croscarmellose Sodium | 10.00 mg | 6.67% |
| Total Tablet | 150.0 mg | 100.0% |

Tablet 2: Immediate/Modified Release
Dextromethorphan and Guaifenesin

| Ingredient | mg/tablet | % Weight |
|---|---|---|
| Immediate Release Layer | | |
| Guaifenesin | 85.5 mg | 47.50% |
| Dextromethorphan HBr | 6.75 mg | 3.75% |
| Microcrystalline Cellulose | 78.77 mg | 43.76% |
| Hypromellose | 4.50 mg | 2.50% |
| Sodium Starch Glycolate | 3.58 mg | 1.99% |
| Mg Stearate | 0.90 mg | 0.50% |
| Total Layer | 180.00 mg | 100.00% |
| Modified Release Layer | | |
| Guaifenesin | 514.50 mg | 88.83% |
| Dextromethorphan HBr | 23.25 mg | 4.03% |
| Hypromellose | 27.50 mg | 4.75% |
| Carbomer | 8.25 mg | 1.42% |
| Colourant | 0.22 mg | 0.04% |
| Mg Stearate | 5.50 mg | 0.95% |
| Total Layer | 579.22 mg | 100.00% |
| Total Tablet | 759.22 mg | 100.0% |

Example 10

Tablet 1: Naproxen

| Ingredient | mg/tablet | % Weight |
|---|---|---|
| Naproxen Sodium | 110 mg | 73.33% |
| Microcrystalline Cellulose | 14.5 mg | 9.67% |
| Povidone | 4.75 mg | 3.17% |
| Mg Stearate | 0.75 mg | 0.7% |
| Lactose | 10.00 mg | 6.67% |
| Croscarmellose Sodium | 10.00 mg | 6.67% |
| Total Tablet | 150.0 mg | 100.0% |

Tablet 2: Immediate/Modified Release
Dextromethorphan and Guaifenesin

| Ingredient | mg/tablet | % Weight |
|---|---|---|
| Immediate Release Layer | | |
| Guaifenesin | 76.00 mg | 47.50% |
| Dextromethorphan HBr | 6.00 mg | 3.75% |
| Microcrystalline Cellulose | 70.02 mg | 43.76% |
| Hypromellose | 4.00 mg | 2.50% |
| Sodium Starch Glycolate | 3.18 mg | 1.99% |
| Mg Stearate | 0.80 mg | 0.50% |
| Total Layer | 160.00 mg | 100.00% |
| Modified Release Layer | | |
| Guaifenesin | 424.00 mg | 91.74% |
| Dextromethorphan HBr | 24.00 mg | 5.19% |
| Carbomer | 9.90 mg | 2.14% |
| Colourant | 0.26 mg | 0.06% |
| Mg Stearate | 4.00 mg | 0.87% |
| Total Layer | 462.16 mg | 100.00% |
| Total Tablet | 622.16 mg | 100.0% |

Example 11

Tablet 1: Naproxen

| Ingredient | mg/tablet | % Weight |
|---|---|---|
| Naproxen Sodium | 110 mg | 72.37% |
| Microcrystalline Cellulose | 9.25 mg | 6.09% |
| Povidone | 4.75 mg | 3.13% |
| Mg Stearate | 1.00 mg | 0.66% |
| Sodium Lauryl Sulphate | 25.00 mg | 16.45% |
| Croscarmellose Sodium | 2.00 mg | 1.32% |
| Total Tablet | 150.0 mg | 100.0% |

Tablet 2: Immediate/Modified Release
Dextromethorphan and Guaifenesin

| Ingredient | mg/tablet | % Weight |
|---|---|---|
| Immediate Release Layer | | |
| Guaifenesin | 85.5 mg | 47.50% |
| Dextromethorphan HBr | 6.75 mg | 3.75% |
| Microcrystalline Cellulose | 78.77 mg | 43.76% |
| Hypromellose | 4.50 mg | 2.50% |

-continued

Tablet 2: Immediate/Modified Release Dextromethorphan and Guaifenesin

| Ingredient | mg/tablet | % Weight |
|---|---|---|
| Sodium Starch Glycolate | 3.58 mg | 1.99% |
| Mg Stearate | 0.90 mg | 0.50% |
| Total Layer | 180.00 mg | 100.00% |
| Modified Release Layer | | |
| Guaifenesin | 514.50 mg | 88.83% |
| Dextromethorphan HBr | 23.25 mg | 4.03% |
| Hypromellose | 27.50 mg | 4.75% |
| Carbomer | 8.25 mg | 1.42% |
| Colourant | 0.22 mg | 0.04% |
| Mg Stearate | 5.50 mg | 0.95% |
| Total Layer | 579.22 mg | 100.00% |
| Total Tablet | 759.22 mg | 100.0% |

Example 12

Tablet 1: Naproxen

| Ingredient | mg/tablet | % Weight |
|---|---|---|
| Naproxen Sodium | 110 mg | 72.37% |
| Microcrystalline Cellulose | 9.25 mg | 6.09% |
| Povidone | 4.75 mg | 3.13% |
| Mg Stearate | 1.00 mg | 0.66% |
| Sodium Lauryl Sulphate | 25.00 mg | 16.45% |
| Croscarmellose Sodium | 2.00 mg | 1.32% |
| Total Tablet | 150.0 mg | 100.0% |

Tablet 2: Immediate/Modified Release Dextromethorphan and Guaifenesin

| Ingredient | mg/tablet | % Weight |
|---|---|---|
| Immediate Release Layer | | |
| Guaifenesin | 76.00 mg | 47.50% |
| Dextromethorphan HBr | 6.00 mg | 3.75% |
| Microcrystalline Cellulose | 70.02 mg | 43.76% |
| Hypromellose | 4.00 mg | 2.50% |
| Sodium Starch Glycolate | 3.18 mg | 1.99% |
| Mg Stearate | 0.80 mg | 0.50% |
| Total Layer | 160.00 mg | 100.00% |
| Modified Release Layer | | |
| Guaifenesin | 424.00 mg | 91.74% |
| Dextromethorphan HBr | 24.00 mg | 5.19% |
| Carbomer | 9.90 mg | 2.14% |
| Colourant | 0.26 mg | 0.06% |
| Mg Stearate | 4.00 mg | 0.87% |
| Total Layer | 462.16 mg | 100.00% |
| Total Tablet | 622.16 mg | 100.0% |

Example 13—Composite Tablet

| Ingredient | mg/tablet | % Weight |
|---|---|---|
| Immediate Release Layer | | |
| Guaifenesin | 140 mg | 28.58% |
| Dextromethorphan HBr | 8 mg | 1.63% |
| Naproxen Sodium | 110 mg | 22.45% |
| Microcrystalline Cellulose | 60 mg | 12.24% |
| Povidone | 11 mg | 2.25% |
| Croscarmellose sodium | 26 mg | 5.31% |
| Crospovidone | 9.8 mg | 2.00% |
| Sodium lauryl sulfate | 25 mg | 5.10% |
| Bicarbonate | 100 mg | 20.41% |
| Mg Stearate | 0.1 mg | 0.02% |
| Total Tablet | 489.9 mg | 100.0% |
| Modified Release Layer | | |
| Guaifenesin | 460 mg | 84.73% |
| Dextromethorphan HBr | 22 mg | 4.05% |
| Hypromellose | 28 mg | 5.16% |
| Hydroxy ethyl cellulose | 14 mg | 2.58% |
| Microcrystalline Cellulose | 17 mg | 3.13% |
| Colourant | 0.1 mg | 0.02% |
| Mg Stearate | 1.8 mg | 0.33% |
| Total Layer | 542.9 mg | 100.0% |

Example 14—Composite Tablet

| Ingredient | mg/tablet | % Weight |
|---|---|---|
| Immediate Release Layer | | |
| Guaifenesin | 200 mg | 45.25% |
| Dextromethorphan HBr | 10 mg | 2.26% |
| Naproxen Sodium | 110 mg | 24.89% |
| Microcrystalline Cellulose | 45 mg | 10.18% |
| Povidone | 11 mg | 2.49% |
| Crospovidone | 65 mg | 14.71% |
| Mg Stearate | 1 mg | 0.23% |
| Total Tablet | 442 mg | 100.0% |
| Modified Release Layer | | |
| Guaifenesin | 400 mg | 84.54% |
| Dextromethorphan HBr | 20 mg | 4.23% |
| Hypromellose | 24.5 mg | 5.18% |
| Hydroxy ethyl cellulose | 12.25 mg | 2.59% |
| Microcrystalline Cellulose | 14.75 mg | 3.12% |
| Colourant | 0.1 mg | 0.02% |
| Mg Stearate | 1.55 mg | 0.33% |
| Total Layer | 473.15 mg | 100.0% |

Example 15—Composite Tablet

| Ingredient | mg/tablet | % Weight |
|---|---|---|
| Immediate Release Layer | | |
| Guaifenesin | 95 mg | 24.26% |
| Dextromethorphan HBr | 7.5 mg | 1.92% |
| Naproxen Sodium | 110 mg | 28.09% |
| Microcrystalline Cellulose | 60 mg | 15.32% |
| Povidone | 11 mg | 2.81% |
| Croscarmellose sodium | 15 mg | 3.83% |
| Crospovidone | 8.00 mg | 2.00% |

| Ingredient | mg/tablet | % Weight |
|---|---|---|
| Sodium Lauryl Sulfate | 25 mg | 5.10% |
| Sodium Bicarbonate | 60 mg | 20.41% |
| Mg Stearate | 0.1 mg | 0.03% |
| Total Layer | 391.6 mg | 100.0% |
| Modified Release Layer | | |
| Guaifenesin | 505 mg | 89.35% |
| Dextromethorphan HBr | 22.5 mg | 3.98% |
| Hypromellose | 25 mg | 4.42% |
| Carbomer | 7.5 mg | 1.33% |
| Colourant | 0.2 mg | 0.04% |
| Mg Stearate | 5.0 mg | 0.88% |
| Total Layer | 565.2 mg | 100.0% |

Example 16—Composite Tablet

| Ingredient | mg/tablet | % Weight |
|---|---|---|
| Immediate Release Layer | | |
| Guaifenesin | 95 mg | 27.34% |
| Dextromethorphan HBr | 7.5 mg | 2.16% |
| Naproxen Sodium | 110 mg | 31.65% |
| Microcrystalline Cellulose | 75 mg | 21.58% |
| Povidone | 11 mg | 3.17% |
| Croscarmellose sodium | 40 mg | 11.51% |
| Crospovidone | 8.00 mg | 2.30% |
| Mg Stearate | 1 mg | 0.29% |
| Total | 347.5 mg | 100.0% |
| Modified Release Layer | | |
| Guaifenesin | 505 mg | 89.35% |
| Dextromethorphan HBr | 22.5 mg | 3.98% |
| Hypromellose | 25 mg | 4.42% |
| Carbomer | 7.5 mg | 1.33% |
| Colourant | 0.2 mg | 0.04% |
| Mg Stearate | 5.0 mg | 0.88% |
| Total Layer | 565.2 mg | 100.0% |

Example 17—Composite Tablet

| Ingredient | mg/tablet | % Weight |
|---|---|---|
| Immediate Release Layer | | |
| Guaifenesin | 95 mg | 24.32% |
| Dextromethorphan HBr | 7.5 mg | 1.92% |
| Naproxen Sodium | 110 mg | 28.16% |
| Microcrystalline Cellulose | 60 mg | 15.36% |
| Povidone | 11 mg | 2.82% |
| Croscarmellose sodium | 22 mg | 5.63% |
| Sodium Lauryl Sulphate | 25.00 mg | 6.40% |
| Sodium Bicarbonate | 60.00 mg | 15.36% |
| Mg Stearate | 0.1 mg | 0.03% |
| Total | 390.6 mg | 100.0% |
| Modified Release Layer | | |
| Guaifenesin | 505 mg | 89.35% |
| Dextromethorphan HBr | 22.5 mg | 3.98% |
| Hypromellose | 25 mg | 4.42% |
| Carbomer | 7.5 mg | 1.33% |
| Colourant | 0.2 mg | 0.04% |
| Mg Stearate | 5.0 mg | 0.88% |
| Total Layer | 565.2 mg | 100.0% |

Example 18—Composite Tablet

| Ingredient | mg/tablet | % Weight |
|---|---|---|
| Immediate Release Layer | | |
| Guaifenesin | 95 mg | 27.98% |
| Dextromethorphan HBr | 7.5 mg | 2.21% |
| Naproxen Sodium | 110 mg | 32.40% |
| Microcrystalline Cellulose | 75 mg | 22.09% |
| Povidone | 11 mg | 3.24% |
| Croscarmellose sodium | 40 mg | 11.78% |
| Mg Stearate | 1 mg | 0.29% |
| Total | 339.5 mg | 100.0% |
| Modified Release Layer | | |
| Guaifenesin | 505 mg | 89.35% |
| Dextromethorphan HBr | 22.5 mg | 3.98% |
| Hypromellose | 25 mg | 4.42% |
| Carbomer | 7.5 mg | 1.33% |
| Colourant | 0.2 mg | 0.04% |
| Mg Stearate | 5.0 mg | 0.88% |
| Total Layer | 565.2 mg | 100.0% |

The tablets of the example embodiments of the present invention can be made using standard tableting procedures well-known to the person skilled in the art.

The bi-layer tablet may be manufactured according to any method known to those of skill in the art. The resulting tablet may comprise the two portions compressed against one another so that the face of each portion is exposed as either the top or bottom of the tablet, or the resulting tablet may comprise the sustained release portion in the centre coated by the immediate release portion so that only the immediate release portion is exposed. In a preferred embodiment, a bi-layer tablet of the present invention comprises the two portions compressed against one another so that the face of each portion is exposed.

The final dosage form can be made by inserting both the immediate-release naproxen tablet and the immediate-release/sustained or modified release guaifenesin/dextromethorphan tablet into a gelatin capsule which is then sealed. Furthermore, the composite tablets of Examples 3 and 4 are final dosage forms and need not, though they can, be inserted into a suitable capsule.

An advantage of the present invention is that there is provided a composition that provides multi-symptom cough/cold/flu relief for 12 hours. Currently, there are no other products that offer all of these significant benefits to consumers.

A further advantage is that there is provided a composition which comprises naproxen, guaifenesin and dextromethorphan in a single dose yet avoids any impact on the dissolution rate of either guaifenesin or dextromethorphan by naproxen.

The composition of the present invention also provides for more consistent release of both guaifenesin and dextromethorphan when compared to known products in various pH conditions and when exposed to various agitation speeds. For example purposes only, these novel formulations have been shown to improve the consistency of dextromethorphan release after 6 hours by 29% and guaifenesin release after 6 hours by 52% and 71%.

Further modifications and improvements can be made without departing from the scope of the invention described herein.

The invention claimed is:

1. A pharmaceutical composition comprising:
   (a) about 600 mg of guaifenesin;
   (b) about 30 mg of dextromethorphan or a pharmaceutically acceptable salt thereof;
   (c) about 110 mg of naproxen or a pharmaceutically acceptable salt thereof;
   (d) at least 25 mg of hypromellose; and
   (e) at least 12.25 mg of hydroxyethyl cellulose;
   wherein the pharmaceutical composition provides a therapeutic effect in respect of each of guaifenesin, naproxen, and dextromethorphan for 12 hours,
   wherein the pharmaceutical composition is a bilayer tablet comprising an immediate release layer containing about 110 mg of the naproxen and at least 95 mg of the guaifenesin and at least 7.5 mg of the dextromethorphan, wherein the immediate release layer contains none of the hypromellose, and wherein the immediate release layer contains none of the hydroxyethyl cellulose.

2. The pharmaceutical composition of claim 1, further comprising sodium lauryl sulfate and sodium bicarbonate.

3. The pharmaceutical composition of claim 2, wherein the sodium bicarbonate is in an amount of about 60 mg.

4. The pharmaceutical composition of claim 3, wherein the immediate release layer contains all of the sodium lauryl sulfate and about 60 mg of the sodium bicarbonate.

5. A pharmaceutical composition comprising:
   (a) about 600 mg of guaifenesin;
   (b) about 30 mg of dextromethorphan or a pharmaceutically acceptable salt thereof;
   (c) about 110 mg of naproxen or a pharmaceutically acceptable salt thereof;
   (d) sodium lauryl sulfate; and
   (e) about 60 mg of sodium bicarbonate;
   wherein the pharmaceutical composition provides a therapeutic effect in respect of each of guaifenesin, naproxen, and dextromethorphan for 12 hours,
   wherein the pharmaceutical composition is a bilayer tablet comprising an immediate release layer containing about 110 mg of the naproxen and at least 95 mg of the guaifenesin and at least 7.5 mg of the dextromethorphan, wherein the immediate release layer contains all of the sodium lauryl sulfate and about 60 mg of the sodium bicarbonate.

6. The pharmaceutical composition of claim 5, further comprising 1-8% hypromellose by weight of the total composition and 1-3% hydroxyethyl cellulose by weight of the total composition.

7. The pharmaceutical composition of claim 6, wherein the hypromellose is in an amount of at least 25 mg and the hydroxyethyl cellulose is in an amount of at least 12.25 mg.

8. The pharmaceutical composition of claim 7, wherein the immediate release layer contains none of the hypromellose, and wherein the immediate release layer contains none of the hydroxyethyl cellulose.

* * * * *